United States Patent
Sos

(10) Patent No.: US 9,717,888 B2
(45) Date of Patent: Aug. 1, 2017

(54) GUIDEWIRE CLAMP AND INTRODUCER

(71) Applicant: Thomas A. Sos, New York, NY (US)

(72) Inventor: Thomas A. Sos, New York, NY (US)

(*) Notice: Subject to any disclaimer, the term of this patent is extended or adjusted under 35 U.S.C. 154(b) by 0 days.

(21) Appl. No.: 15/005,210

(22) Filed: Jan. 25, 2016

(65) Prior Publication Data

US 2016/0213889 A1 Jul. 28, 2016

Related U.S. Application Data

(60) Provisional application No. 62/140,138, filed on Mar. 30, 2015, provisional application No. 62/121,695, filed on Feb. 27, 2015, provisional application No. 62/107,962, filed on Jan. 26, 2015.

(51) Int. Cl.
| | | |
|---|---|---|
| *A61B 5/00* | (2006.01) | |
| *A61M 25/09* | (2006.01) | |
| *F16B 2/10* | (2006.01) | |
| *A61M 25/00* | (2006.01) | |

(52) U.S. Cl.
CPC .......... *A61M 25/09* (2013.01); *A61M 25/002* (2013.01); *F16B 2/10* (2013.01)

(58) Field of Classification Search
CPC ................ A61M 25/09; A61M 25/002; A61M 25/09041; A61M 2025/09125; A61M 2025/024; A61M 39/284
See application file for complete search history.

(56) References Cited

U.S. PATENT DOCUMENTS

| | | | |
|---|---|---|---|
| 3,993,081 A * | 11/1976 | Cussell | A61M 16/0488 128/207.14 |
| 4,707,906 A | 11/1987 | Posey | |
| D329,698 S | 9/1992 | Loney et al. | |
| 5,279,573 A | 1/1994 | Klosterman | |
| 5,379,489 A * | 1/1995 | Delk | B65D 33/1675 24/30.5 R |
| 5,507,300 A | 4/1996 | Mukai et al. | |
| 5,755,225 A * | 5/1998 | Hutson | A61M 16/0488 128/200.26 |
| 5,830,183 A | 11/1998 | Krieger | |
| 6,047,825 A | 4/2000 | Samuels | |
| 6,488,664 B1 * | 12/2002 | Solomon | A61M 16/0666 24/20 R |
| 7,144,402 B2 | 12/2006 | Kuester, III | |
| 7,886,906 B1 | 2/2011 | Dunn et al. | |
| 8,439,193 B2 | 5/2013 | Koellhofer et al. | |

(Continued)

FOREIGN PATENT DOCUMENTS

CN 203598053 U 5/2014

OTHER PUBLICATIONS

International search report and written opinion dated Jun. 3, 2016 for PCT/US2016/014727.

*Primary Examiner* — Max Hindenburg
(74) *Attorney, Agent, or Firm* — Wilson, Sonsini, Goodrich & Rosati

(57) ABSTRACT

A guidewire for medical procedures can be maintained in a coiled configuration with a clamp. Multiple clamped and coiled guidewires may be stored in a fluid-filled, storage bowl concurrently. Different clamps may have different colors to differentiate the clamps and clamped guidewires. The clamps may be markable to provide additional differentiation. The clamps can further comprise a guidewire introduction funnel and/or a guidewire torquer.

23 Claims, 25 Drawing Sheets

(56) References Cited

U.S. PATENT DOCUMENTS

| | | |
|---|---|---|
| 8,480,597 B2 | 7/2013 | Cornish et al. |
| 8,679,065 B2 | 3/2014 | Schuman et al. |
| 8,801,677 B2 * | 8/2014 | Wallin ................ A61M 39/284 |
| | | 251/10 |
| 8,850,676 B2 * | 10/2014 | Schmitt ........... A61M 25/09041 |
| | | 29/44 |
| 8,968,214 B2 * | 3/2015 | Numata .............. A61M 25/002 |
| | | 600/434 |
| 9,011,351 B2 * | 4/2015 | Hoshinouchi ... A61M 25/09041 |
| | | 600/585 |
| 9,079,008 B2 * | 7/2015 | Ebara .................... A61M 5/168 |
| 9,089,672 B2 * | 7/2015 | Hendriksen ........... A61M 25/02 |
| 9,127,786 B1 * | 9/2015 | Arratia .................. A61M 25/09 |
| 9,498,616 B2 * | 11/2016 | Mathias .............. A61M 39/284 |
| 9,499,318 B2 * | 11/2016 | Christensen ........... B65D 67/02 |
| 2012/0227751 A1 | 9/2012 | Horer |
| 2013/0292365 A1 | 11/2013 | Cornish et al. |
| 2014/0171833 A1 | 6/2014 | Matsuno et al. |
| 2014/0259821 A1 | 9/2014 | Meyerson et al. |

\* cited by examiner

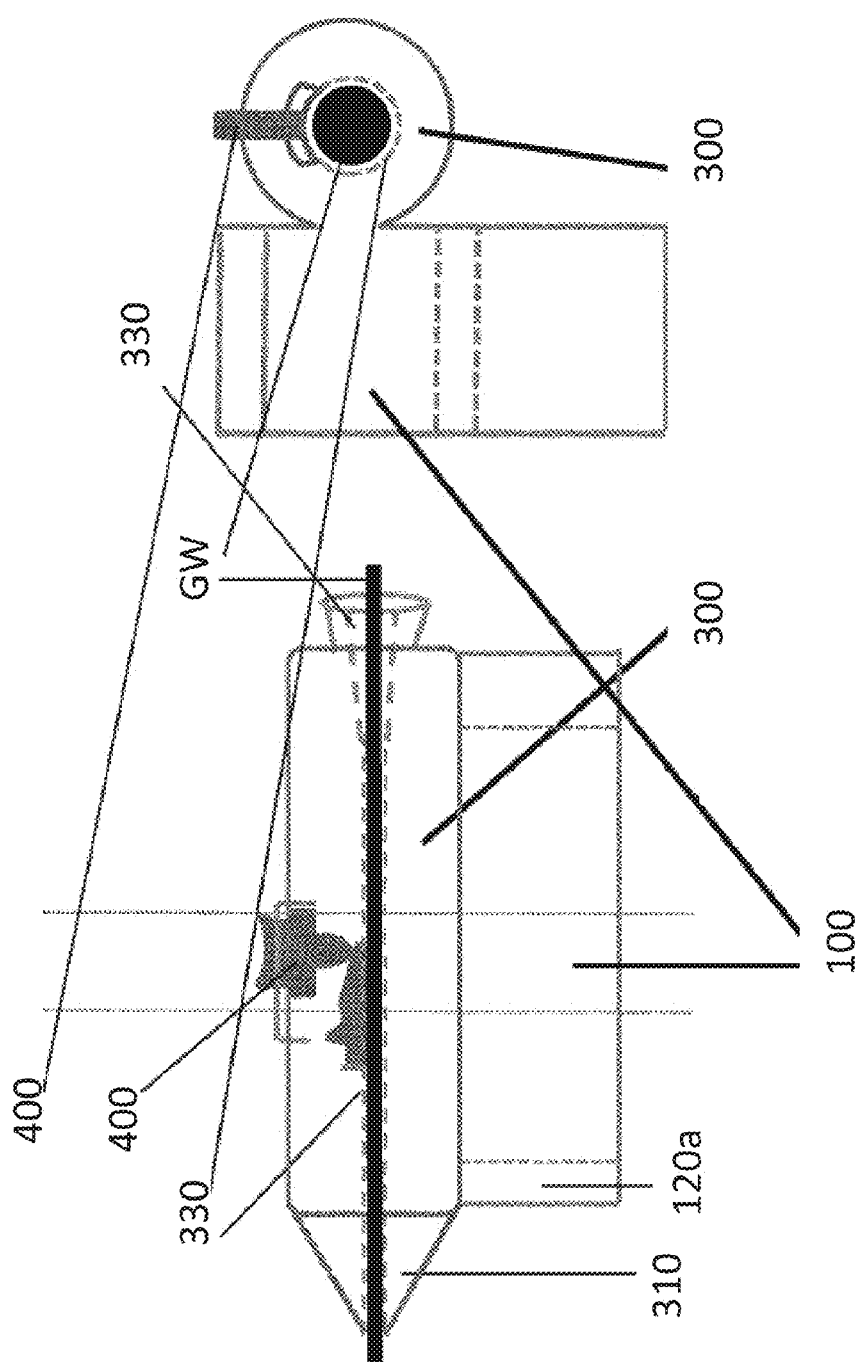

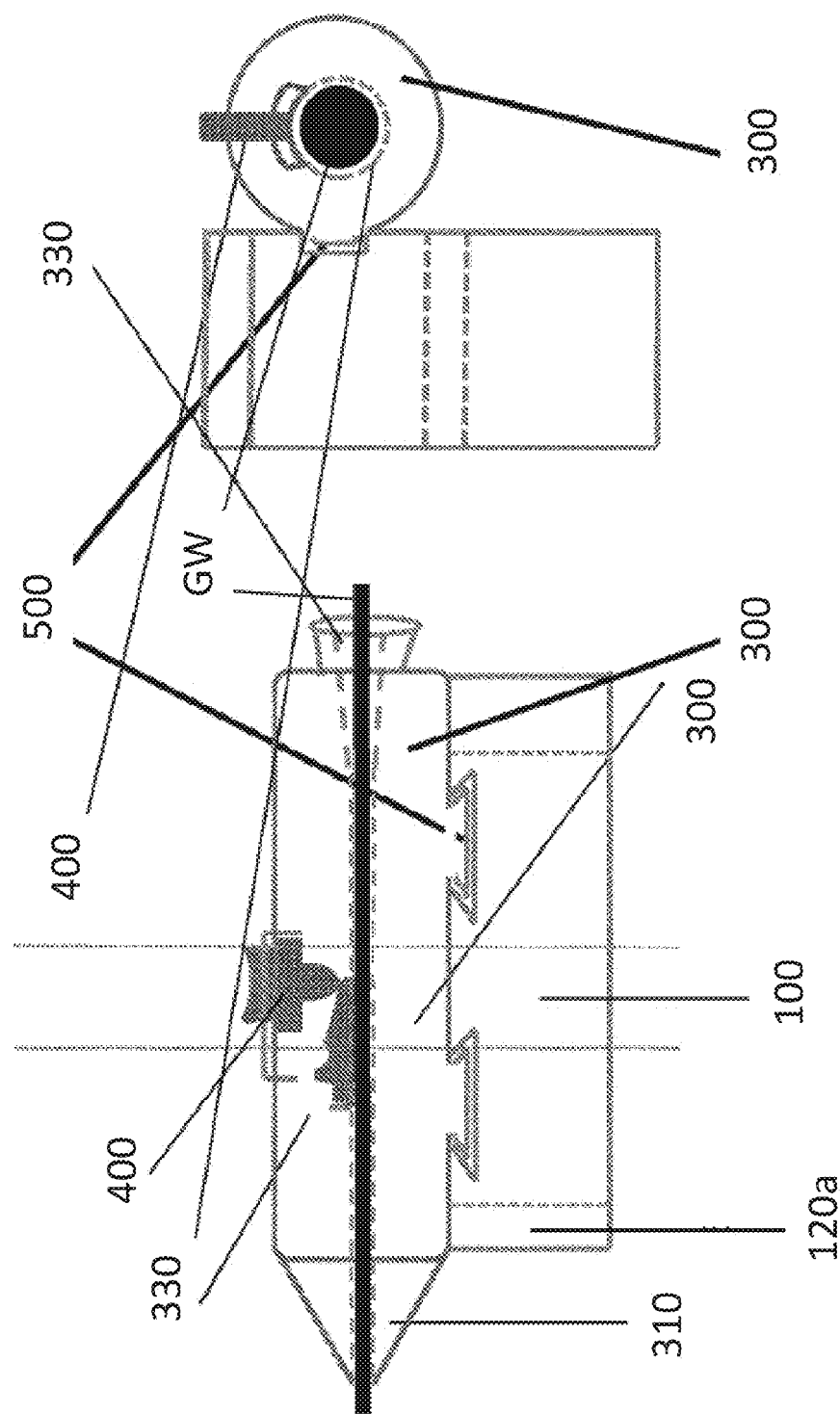

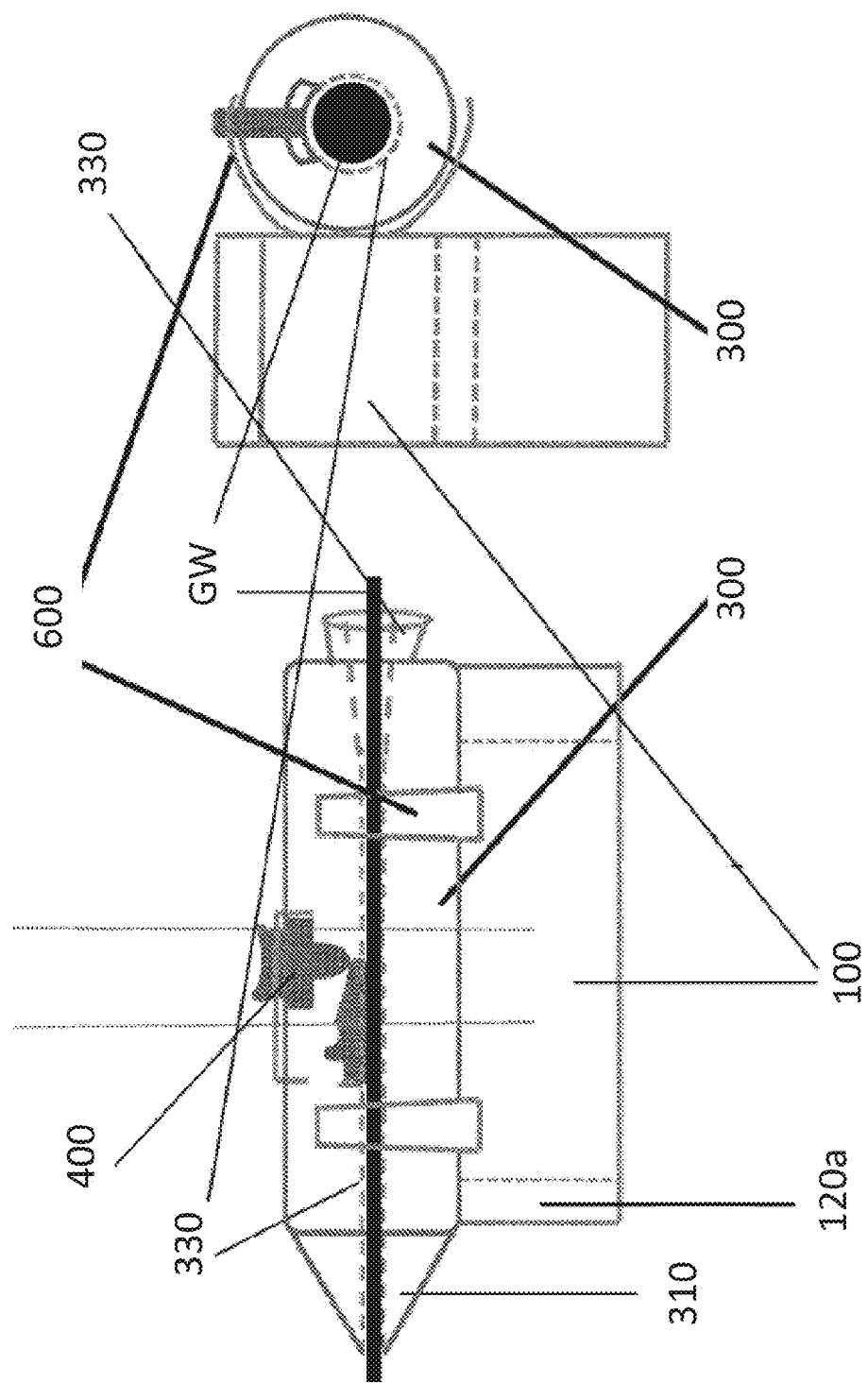

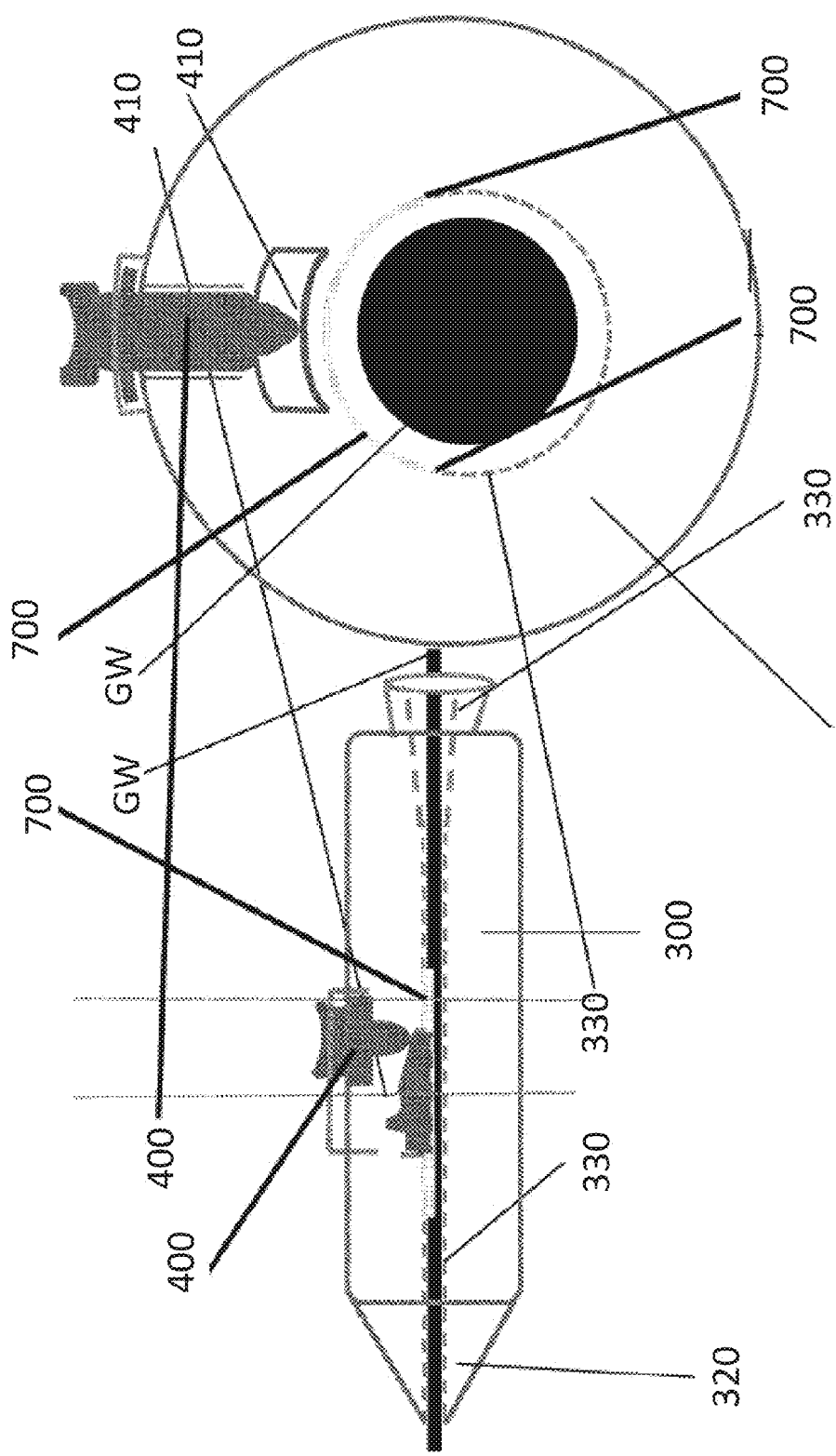

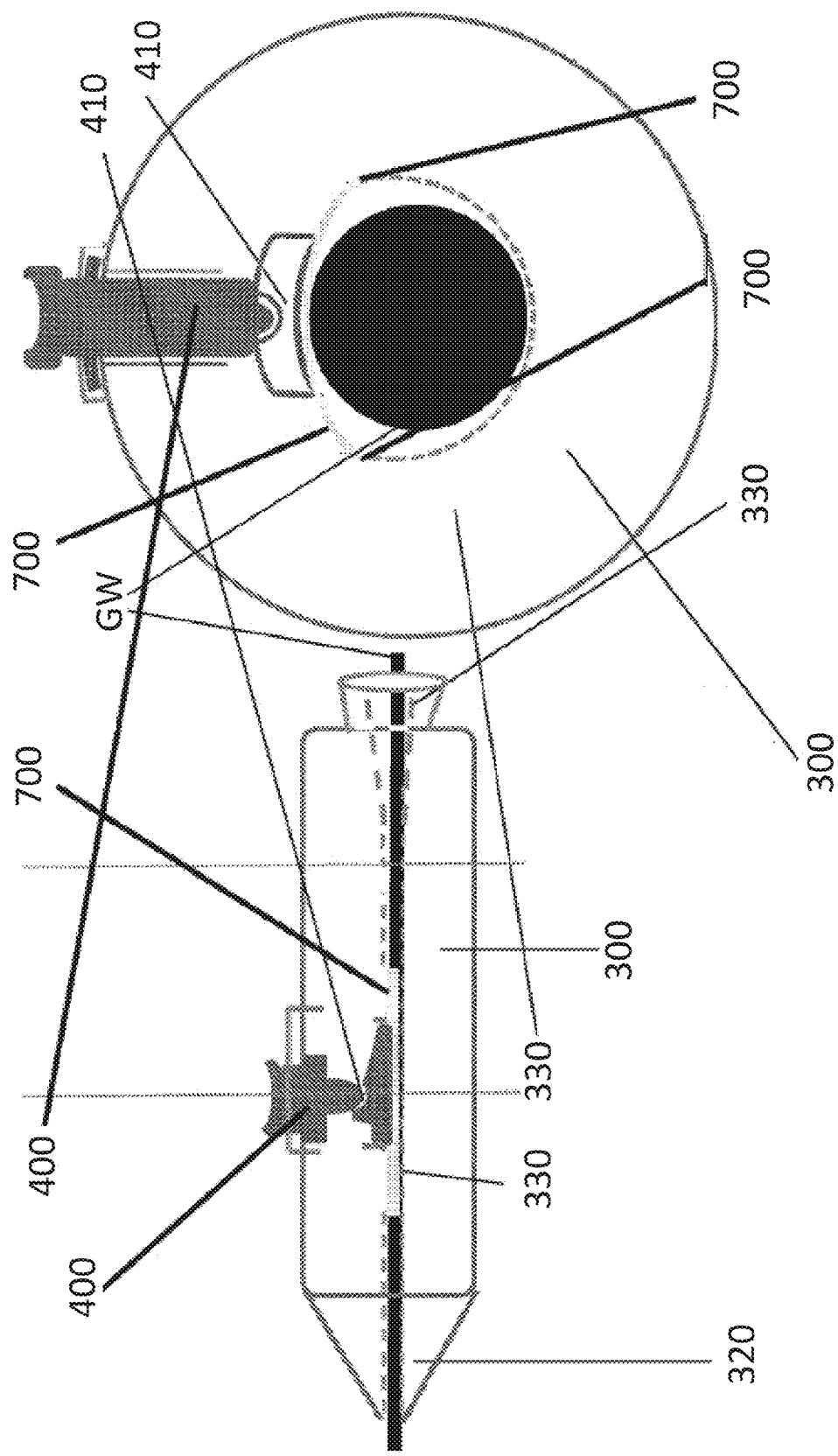

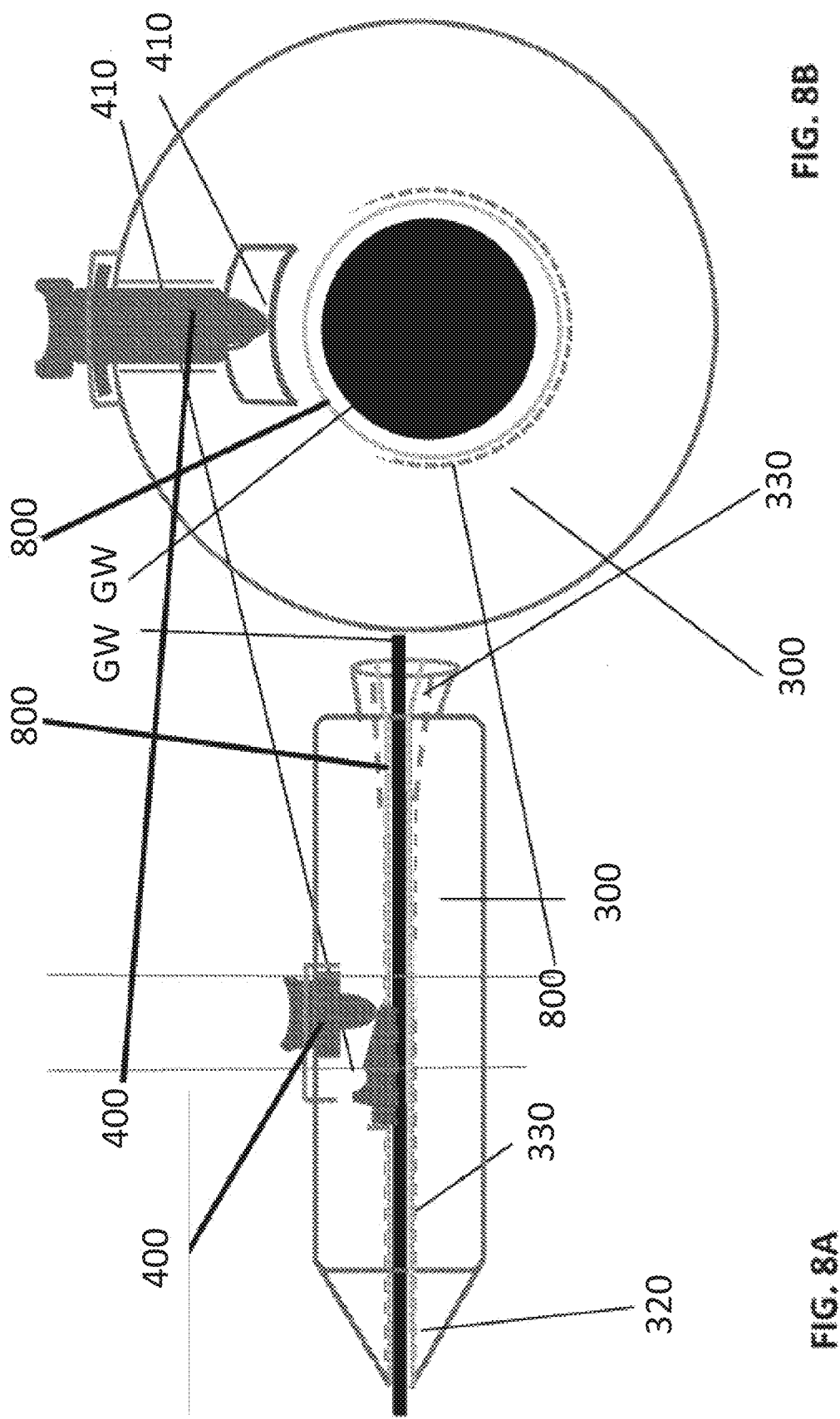

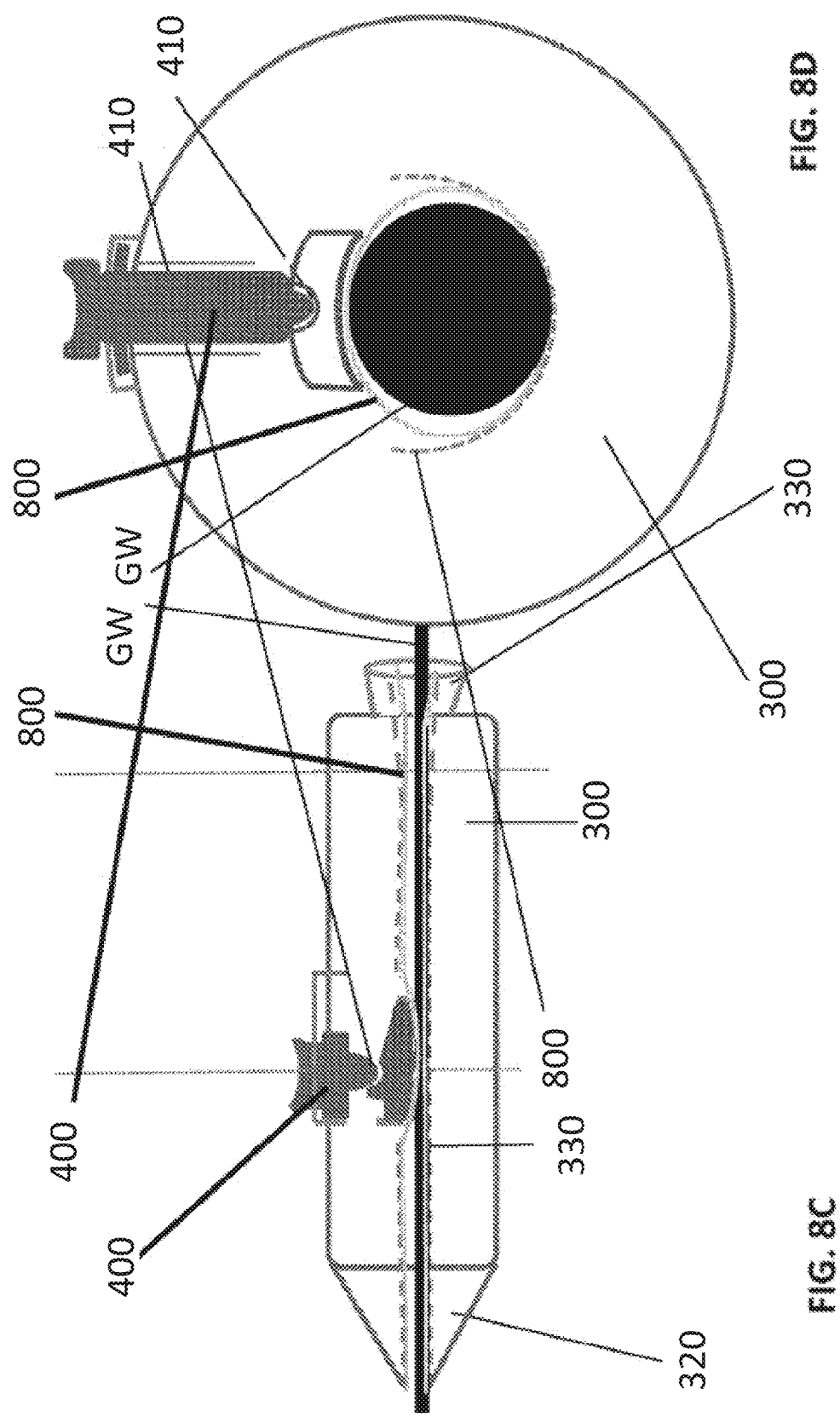

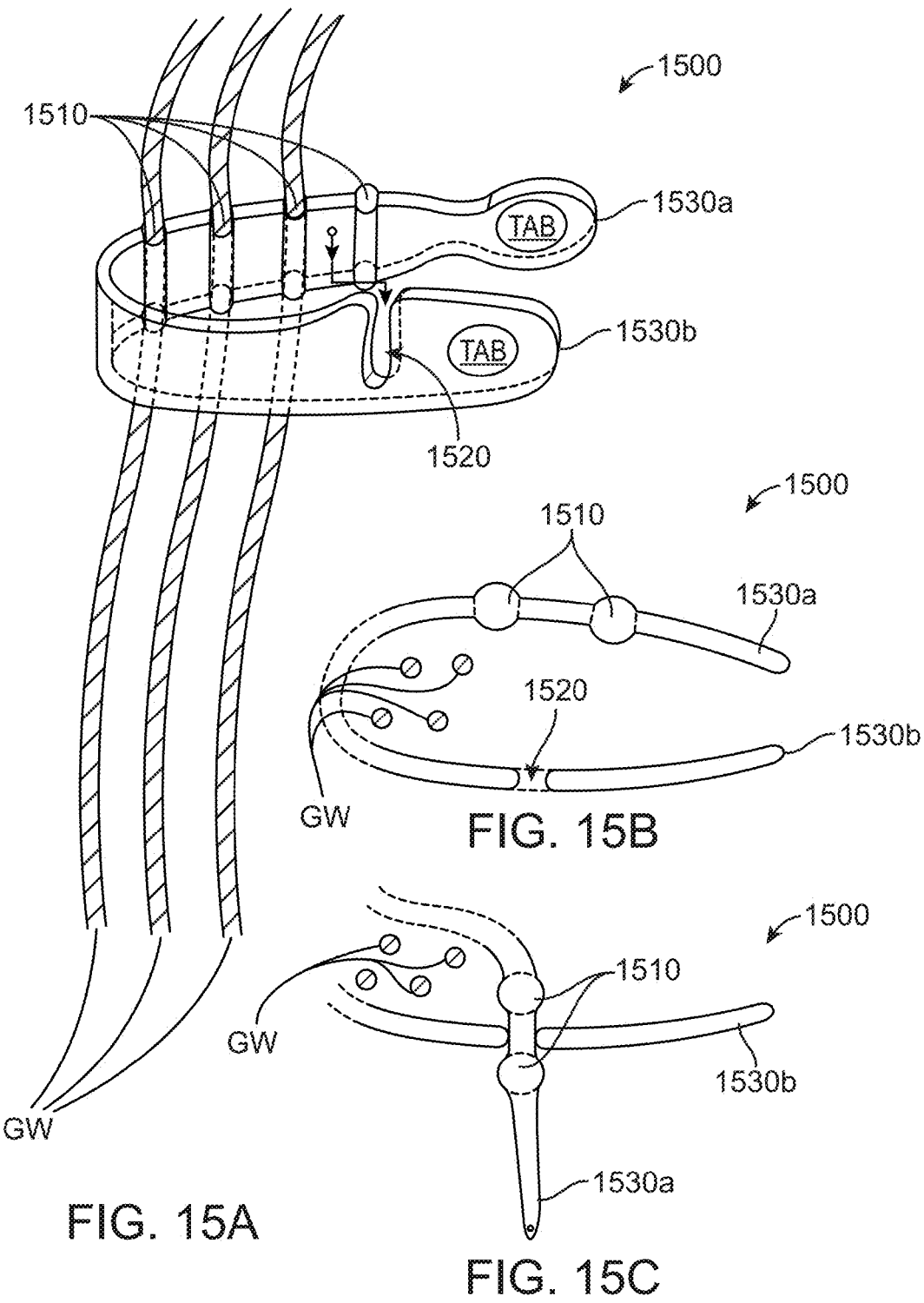

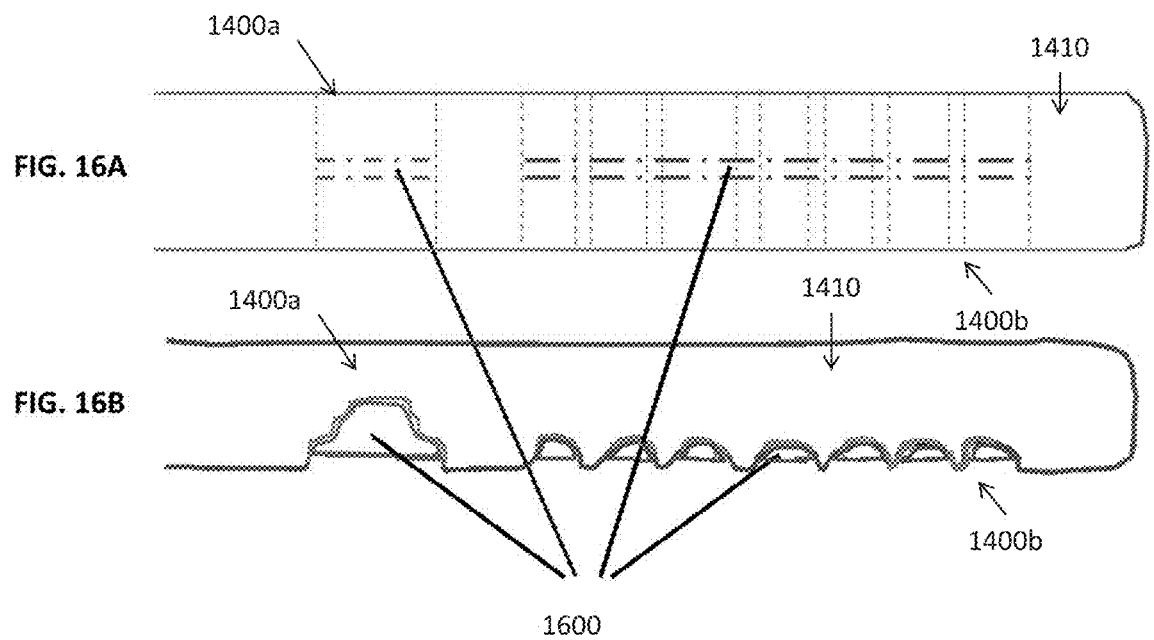

GUIDEWIRE CLAMP AND INTRODUCER

CROSS-REFERENCE TO RELATED APPLICATIONS

This application claims the benefit of U.S. Provisional Application Nos. 62/140,138, filed Mar. 30, 2015, 62/121,695, filed Feb. 27, 2015 and 62/107,962, filed Jan. 26, 2015, the contents of which are fully incorporated herein by reference.

BACKGROUND

The present disclosure relates to medical devices and methods, particularly for the storage of guidewires suitable for use in various medical procedures and for the introduction of these guidewires into the proximal hubs of catheters.

The following references may be of interest: U.S. Publication Nos. 2014/0259821, 2014/0171833, 2013/0292365, and 2012/0227751 and U.S. Pat. Nos. 8,679,065, 8,480,597, 7,886,906, 7,144,402, 6,047,825, 5,830,183, 5,279,573, 4,707,906, and D329698.

SUMMARY

The present disclosure relates to medical devices and methods, particularly for the storage of guidewires suitable for use in various medical procedures. During a medical procedure, for example, guidewires may be coiled and temporarily stored in one or more fluid-filled bowls. In many medical procedures, a single guidewire is used or multiple guidewires may be used concurrently. In such procedures, one or multiple guidewires may be stored between re-use during the same procedure in a coiled configuration where the stiff end of the guidewire is looped under the coiled guidewire loops to secure the loops. However, this technique may often fail as the loops can uncoil spontaneously or can be uncoiled when a medical practitioner attempts to identify and retrieve a specific guidewire from the bowl. With one or more of the coiled wires becoming uncoiled, the guidewire(s) may unravel, straighten, and spontaneously spring out of the sterile fluid filled bowl, becoming potentially contaminated and contaminating the sterile environment. In at least some cases, particularly in a small and crowded fluid filled storage bowl, a medical practitioner may confuse one guidewire with another. Such confusion may be problematic where one guidewire suitable for one application becomes used in a different application. Disclosed herein are devices and methods to temporarily store guidewires in an improved manner so as to address some of these disadvantages.

Aspects of the present disclosure provide color-coded and markable clamps for maintaining a guidewire in a coiled configuration when placed in a storage bowl. Clamps with different coloring and/or different markings made thereon may be used with different guidewires of various diameters and/or design or performance characteristics. The different clamps can help a medical practitioner quickly and easily identify and differentiate between different guidewires in a multi-wire environment.

Aspects of the present disclosure may provide a method of storing one or more guidewires. A guidewire may be wrapped into a coiled configuration. In the coiled configuration, the guidewire may have a coiled portion and a free end portion. The free end portion may comprise a stiff end of the guidewire. The free end portion may be wrapped under the coiled portion. A color-coded, markable clamp may be placed over the free end portions and/or a part of the coiled portion. The clamp may maintain the guidewire in the coiled configuration. The guidewire and clamp placed thereover may be placed in a fluid-filled storage bowl. The method may be repeated for a second or further guidewire to be placed in the same or different storage bowl. To distinguish the guidewires, the second or further clamp may have a different color than the first guidewire or may be marked in a different manner. In some embodiments, the first and/or second portion or jaw of the clamp may comprise an introducer shaped as a funnel. The funnel may lead to a straight guidewire lumen which leads to a tip tapered on the outside. The tip may be coupled to the hub of a catheter for the introduction of shaped tipped or other guidewires into the inner lumen of the catheter. The first, second, or other guidewire may have a diameter matching the color coding, marking, or labelling of the clamp; and, the lumen of the funnel of the clamp may have a diameter matching that of the guidewire. In this manner, a guidewire of a preselected size can be stored and introduced to a catheter with the same clamp or clamp structure. Further, a grasping mechanism may be actuated to secure the first guidewire relative to the funnel structure of the first clamp to allow the entire structure to function as a guidewire torque device or torquer.

Aspects of the present disclosure may also provide a clamp for facilitating guidewire storage. The clamp may comprise a first portion, a second portion, and a pivotable portion therebetween. The first and second portions may be folded or pivoted relative to one another about the pivotable portion to open or close the clamp. The first and second portions may comprise upper surfaces which may approximate or come into contact with one another when the clamp is closed. The upper surface of one or more of the first or second portions may comprise surface features to facilitate the capture of the guidewire. For example, the upper surfaces may comprise teeth or be ridged. Alternatively or in combination, the upper surfaces may comprise a high friction material or coating such as rubber, latex, teflon, silicone, or other polymer. The material or coating may be compliant to minimize any damage that may occur to the guidewire as it is clamped. The material and/or coating may be colored and/or may be markable such as with a pen or marker. Where a coating is used, the clamp upper or lower portions may comprise a core made of a harder material such as hardened rubber, silicone, or other polymer. Alternatively, the clamp may be in a single, integral piece made of the high friction and/or compliant material.

The clamp may further comprise a first end coupled to the first portion and a second end opposite the first end and coupled to the second portion. The first and second ends may be removably coupled to one another. For example, the first and second ends may form a latch mechanism. The first end may comprise one or more teeth to capture the second end when the first and second portions are folded or pivoted relative to one another to close the clamp. These teeth may be de-coupled from the second end so that the first and second portions can be folded or pivoted relative to one another to open the clamp. Alternatively or in combination, the first end may have a series of apertures or openings to capture the second end.

The clamp may further comprise a guidewire introducer coupled to one or more of the first or second portions. The guidewire introducer may be removably coupled to a main body of the clamp. The guidewire introducer may have a guidewire lumen, an open proximal funnel end to receive a guidewire and direct it into the guidewire lumen, and a distal tapered tip to couple with a proximal hub of a catheter. The guidewire introducer may further comprise a grasping mechanism to secure the guidewire received in the guidewire lumen.

Aspects of the present disclosure may also provide a kit for facilitating guidewire storage. The kit may include a first clamp and a second clamp. The clamps may be as described as above. The first clamp may have a first color and the second clamp may have a second color different from the first color. One or more of the first or second clamps may be markable. The kit may further include a storage bowl for the guidewires and a set of instructions. One or more of the first or second clamps may comprise a funnel structure integral with its first or second portion or jaw. The funnel structure may have a tip configured to be coupled to a hub of a catheter of the same internal diameter as marked or indicated by the respective clamp. The funnel structure may further comprise a grasper mechanism to secure a guidewire received in the funnel structure. Alternatively or in combination, the funnel structure may be a separate device to be removably coupled to the main body of the one or more clamps.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. It should be noted that the drawings are not to scale and are intended only as an aid in conjunction with the explanations in the following detailed description. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. A better understanding of the features and advantages of the present disclosure will be obtained by reference to the following detailed description that sets forth illustrative embodiments, in which the principles of the present disclosure are utilized, and the accompanying drawings of which:

FIG. 4A shows a top section view of a single piece guidewire clamp with an integrated introducer funnel and torquer, according to many embodiments.

FIG. 4B shows a back section view of the single piece guidewire clamp of FIG. 4A.

FIG. 5A shows a top section view of a two piece guidewire clamp with a detachable introducer funnel and torquer, according to many embodiments.

FIG. 5B shows a back section view of the two piece guidewire clamp of FIG. 5A.

FIG. 6A shows a top section view of another two piece guidewire clamp with a detachable introducer funnel and torquer, according to many embodiments.

FIG. 6B shows a back section view of the two piece guidewire clamp of FIG. 6A.

FIG. 7A shows a top section view of another guidewire introducer funnel and torquer in an open configuration, according to many embodiments.

FIG. 7B shows a cross-sectional view of the guidewire introducer funnel and torquer of FIG. 7A in the open configuration.

FIG. 7C shows a top section view of the guidewire introducer funnel and torquer of FIG. 7A in a closed configuration, according to many embodiments.

FIG. 7D shows a cross-sectional view of the guidewire introducer funnel and torquer of FIG. 7A in the closed configuration.

FIG. 8A shows a top section view of another guidewire introducer funnel and torquer in an open configuration, according to many embodiments.

FIG. 8B shows a cross-sectional view of the guidewire introducer funnel and torquer of FIG. 8A in 8A in the open configuration.

FIG. 8C shows a top section view of the guidewire introducer funnel and torquer of FIG. 8A in a closed configuration.

FIG. 8D shows a cross-sectional view of the guidewire introducer fund and torquer of FIG. 8A in the closed configuration.

FIG. 15A shows a perspective view of another guidewire clamp capturing multiple loops of a guidewire, according to many embodiments.

FIG. 15B shows a top view of the guidewire clamp of FIG. 15A in an open configuration.

FIG. 15C shows a top view of the guidewire clamp of FIG. 15B in a closed configuration.

FIG. 16A shows a bottom view of the jaw of a guidewire clamp comprising a crushable, "thin" membrane, according to many embodiments.

FIG. 16B shows a side view of the jaw of the guidewire clamp of FIG. 16A.

DETAILED DESCRIPTION

Figure 1A:
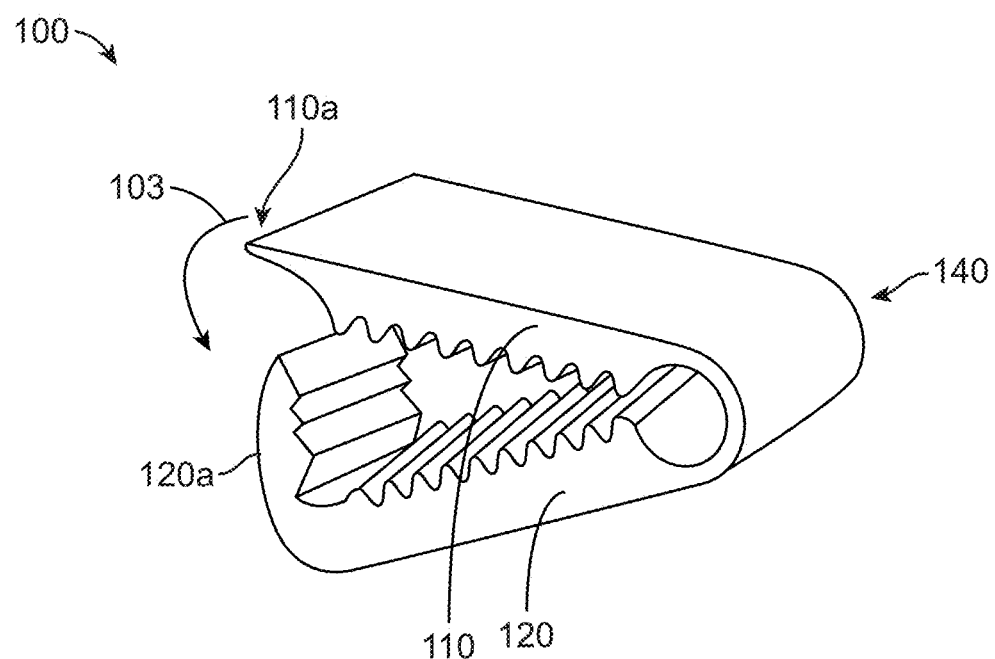
FIG. 1A shows a perspective view of a guidewire clamp according to many embodiments.
Figure 1B:
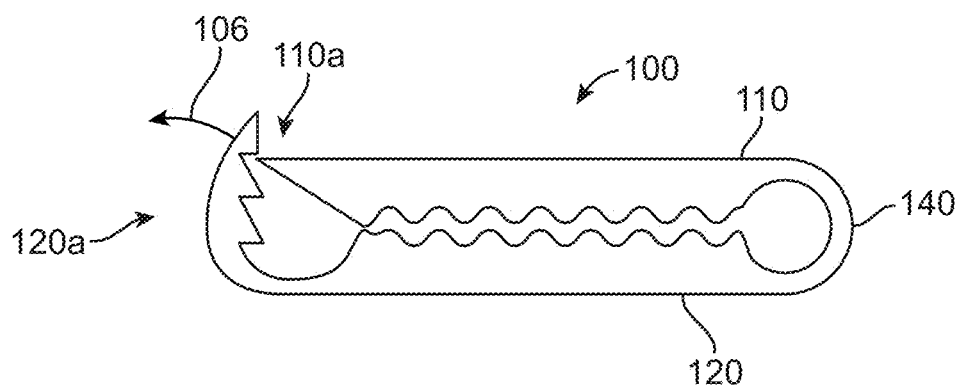
FIG. 1B shows a side view of the guidewire clamp of FIG. 1A.
Figure 1C:
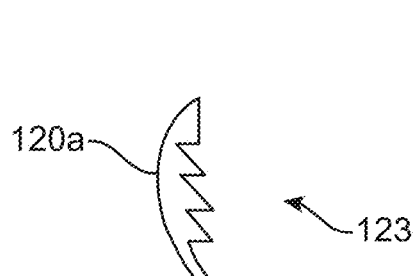
FIG. 1C shows a side view toothed extension of an end of the guidewire clamp of FIG. 1A.
Figure 1D:
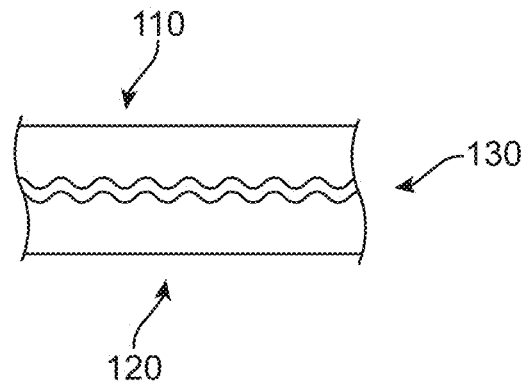
FIG. 1D shows a magnified side view of an embodiment of the toothed jaws of the guidewire clamp of FIG. 1A.
Figure 1E:
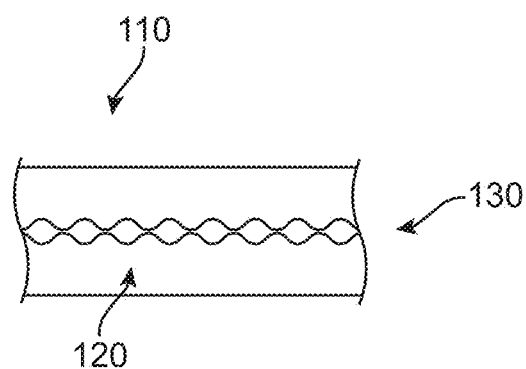
FIG. 1E shows a magnified side view of an embodiment of the toothed jaws of the guidewire clamp of FIG. 1A.
Figure 1F:
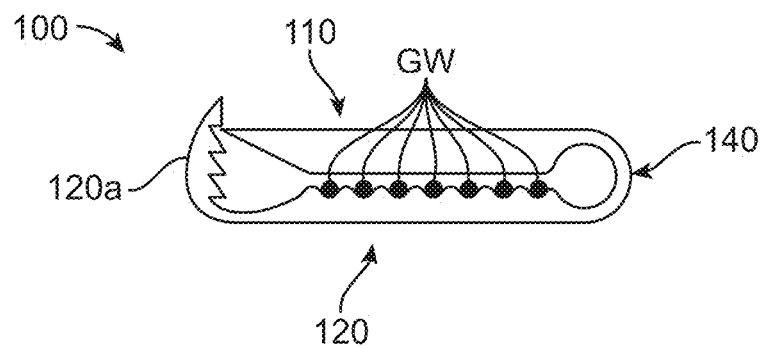
FIG. 1F shows a side view of the guidewire clamp of FIG. 1A closed to grasp multiple loops of a guidewire.

FIGS. 1A-1F shows various views of a guidewire clamp 100 according to many embodiments. The guidewire clamp 100 may comprise two jaws—an upper jaw 110 and a lower jaw 120—that may be closed against one another to trap a coiled guidewire GW between the teeth of the jaws 110, 120 (FIG. 1F). As shown in FIG. 1B, the guidewire clamp 100 may be about 1.0 to about 1.5 cm in length, about 1.0 to about 1.5 cm in height, and about 2.5 cm in total width when closed. The teeth 130 of the jaws 110, 120 may fit with one another when closed (FIG. 1D) or may oppose one another (FIG. 1E). The jaws 110, 120 may pivot relative to one another about a pivot region 135, which may be relatively thin, toothless, and flexible (FIGS. 1A, 1B, 1F). The lower jaw 120 may comprise an extension 120a which may comprise one or more teeth 123 and which may be curved toward the end 110a of the upper jaw 110 when the jaws 110, 120 are moved toward one another such as in the direction of arrow 103 (FIG. 1A). A tooth pair of the extension 120a may lock onto the extension 110a and the tooth pair may be selected to determine how tightly the jaws 110, 120 are locked with one another. The extension 120a may be peeled away from the end 110a such as in a direction 106 (FIG. 1B) to de-couple the ends of the jaws 110, 120 from one another. Alternatively or in combination, the upper jaw 110 may have an extension with teeth to lock onto the end of the lower jaw 120.

In some embodiments, the guidewire clamp 100 may lack teeth for the top and/or bottom jaw. The guidewire clamp 100 may be made of various materials, such as a soft rubber, teflon, or other polymers. The entire guidewire clamp 100 may be made of a single material or of a combination of various materials. The guidewire clamp 100 may be color coded and/or comprise a markable surface for identification. A plurality of the guidewire clamps 100 may be provided in a kit, where different guidewire clamps of the kit for different diameter guidewires may have different colors. In some embodiments, the clamp 100 may further comprise an integral guidewire introducer lumen or funnel with a diameter matching that of the guidewire the clamp 100 is color coded or marked to identify. In some embodiments, the clamp 100 may further comprise an integral guidewire torque device or torquer as a part of the guidewire introducer lumen or funnel.

Figure 2A:
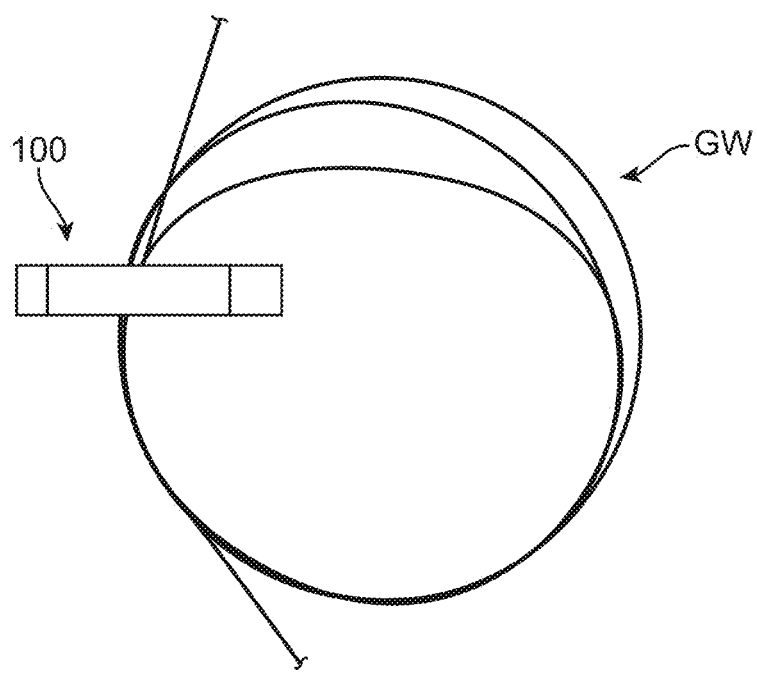
FIGS. 2A and 2B show perspective views of guidewires maintained in a coiled configuration by a guidewire clamp, according to many embodiments.
Figure 2B:
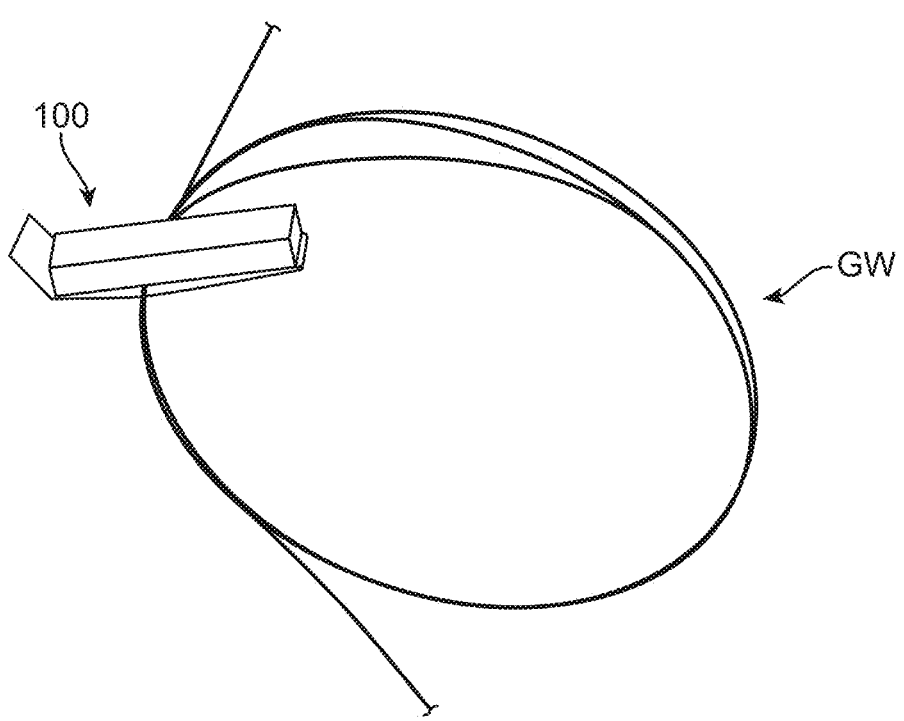

FIGS. 2A and 2B show guidewires GW maintained in a coiled configuration by the guidewire clamp 100, according to many embodiments. The guidewire GW may be formed into a configuration with multiple, circular loops with opposite first and second ends that are straight. The guidewire clamp 100 may grasp the guidewire GW at the circular loops.

Figure 3A:
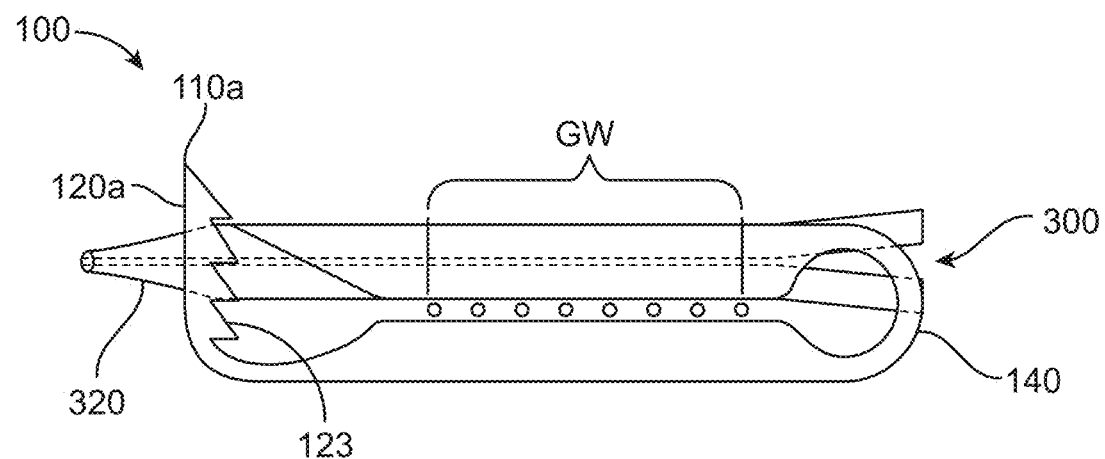
FIG. 3A shows a side section view of a guidewire clamp with a built-in guidewire introducer funnel, according to many embodiments.
Figure 3B:
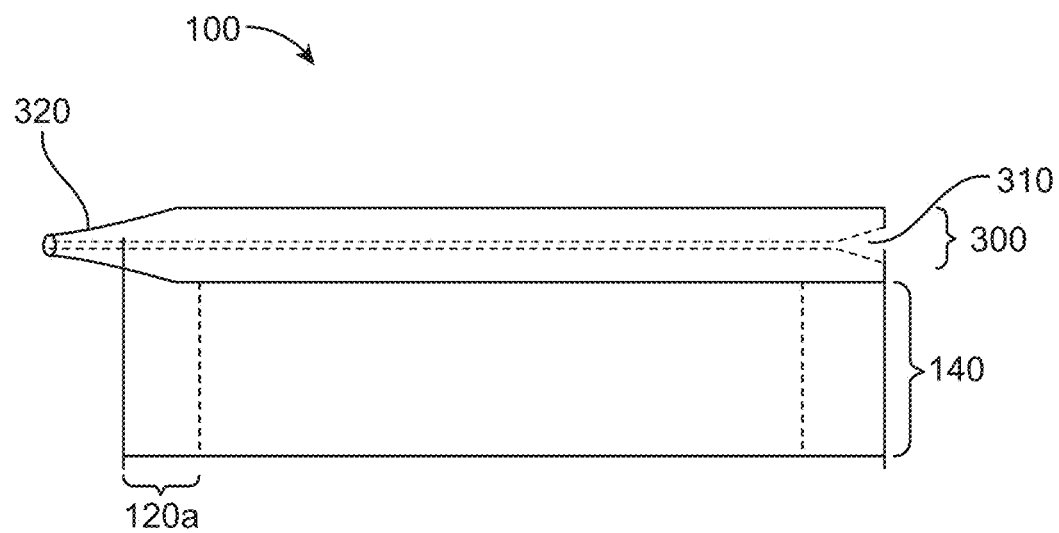
FIG. 3B shows a top section view of the guidewire clamp of FIG. 3A.
Figure 3C:
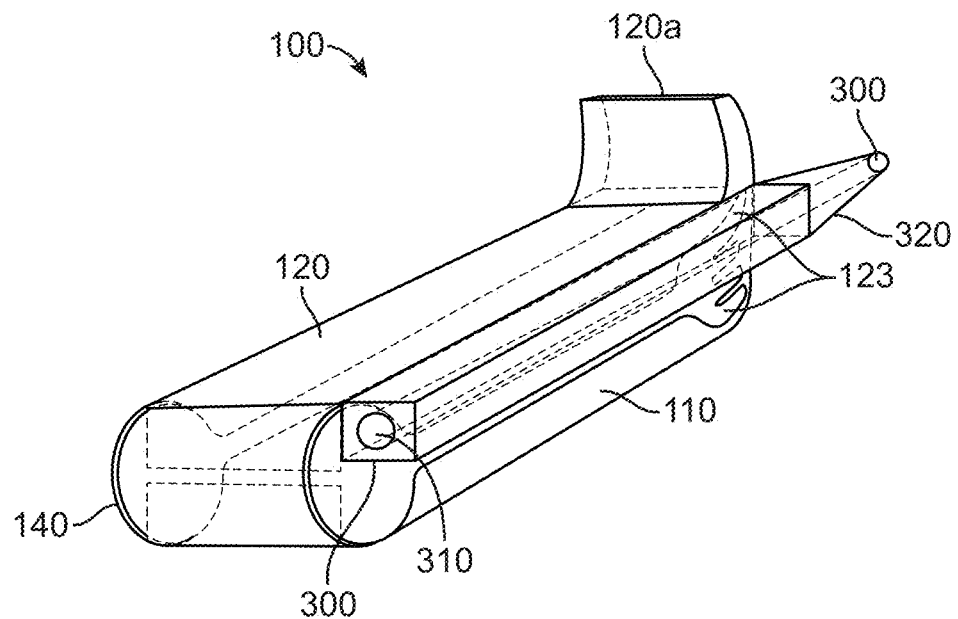
FIG. 3C shows a perspective section view of the guidewire clamp of FIG. 3A.
Figure 3D:
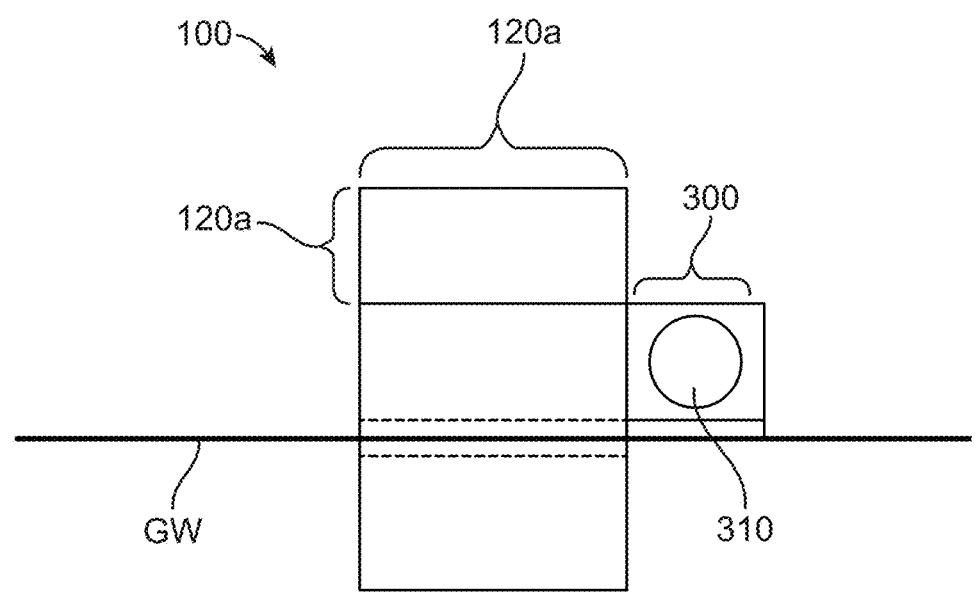
FIG. 3D shows a back view of the guidewire clamp of FIG. 3A.
Figure 3E:
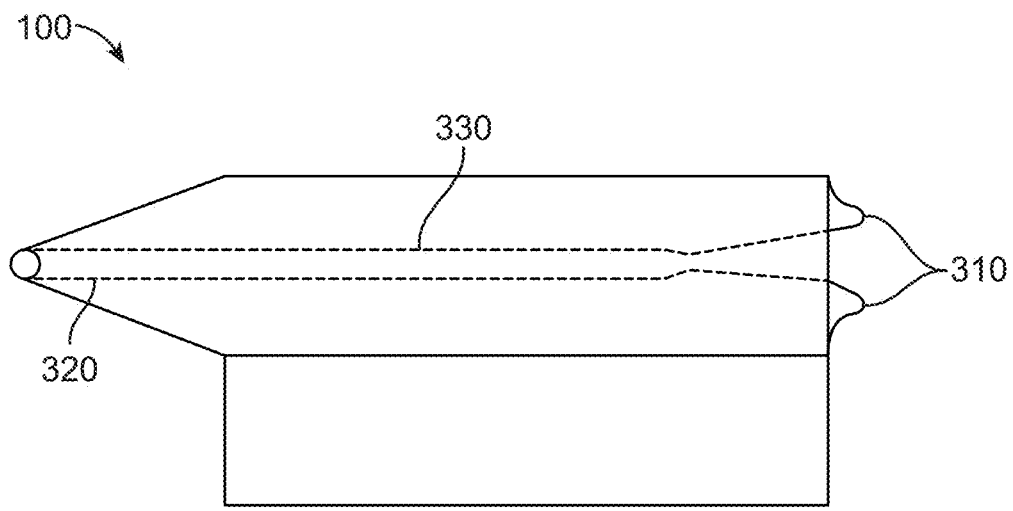
FIG. 3E shows a top section view of the guidewire clamp of FIG. 3A, highlighting the proximal end of the introducer funnel, according to many embodiments.
Figure 3F:
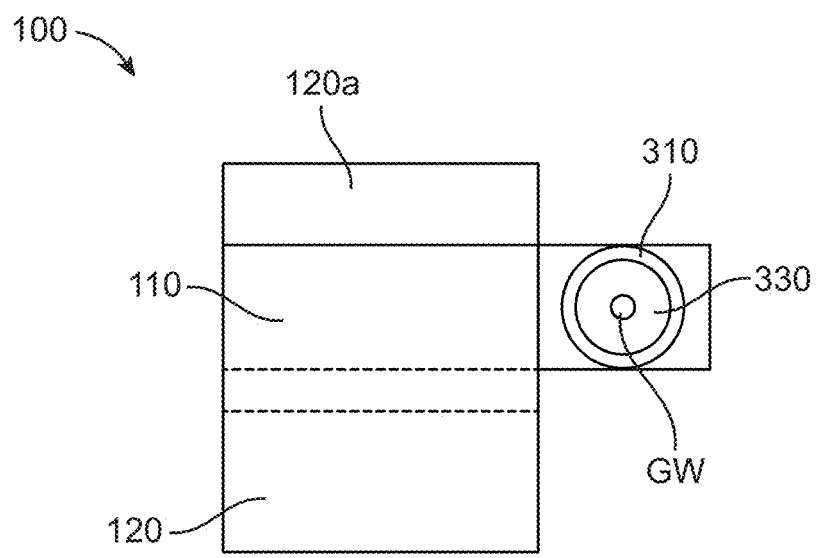
FIG. 3F shows a back section view of the guidewire clamp of FIG. 3A, highlighting the proximal end of the introducer funnel.

FIG. 3A shows a side section view of an embodiment of the guidewire clamp 100 with a built-in guidewire introducer funnel or funnel structure 300, according to many embodiments; FIG. 3B shows the top section view of the same; FIG. 3C shows the perspective section view of the same; FIG. 3D shows the back view of the same; FIG. 3E shows a top section view of the same; and FIG. 3F shows a back view of the same. At the proximal end near the flexible region 140, the funnel structure 300 may have a raised funnel ridge or rim 310 to facilitate introduction of the guidewire GW into a straight, central lumen 330 of the funnel structure 300. The diameter of the straight, central lumen may match the diameter of the guidewire the clamp is color-coded, marked, or otherwise labeled for. At the distal end, the funnel structure 300 may comprise a tapered tip 320 which may couple to a proximal hub of a catheter and its inner lumen. A guidewire GW can be advanced through the lumen of the funnel structure 300 to introduce the guidewire GW to the hub and inner lumen of the catheter. As shown in FIGS. 3C and 3D, the funnel structure 300 may be located on a side of the bottom or top jaws 110, 120, respectively. As shown in FIGS. 3E and 3F, the proximal end of the funnel structure 300 may include a raised funnel ridge or rim 310 to direct the guidewire GW, the leading tip of which is often curved, into the straight, central lumen.

The guidewire clamp 100 as in FIGS. 3A-3F may be suitable for a guidewire GW of a pre-selected size. The guidewire clamp 100 may be color coded, marked, or otherwise labelled to indicate its suitability for the guidewire GW of the pre-selected size. The funnel structure 300 of the guidewire clamp 100, including its central lumen 330 and distal tip 320, may have a size suitable for the guidewire GW to be advanced therethrough to be introduced into a catheter hub and lumen.

FIGS. 4A-12B show further embodiments of the guidewire clamp 100. The guidewire clamp 100 may comprise the guidewire introducer 300 which may also serve as a guidewire introducer/torquer component with the aid of slider compression assembly 400. The guidewire clamp device 100 and/or the guidewire introducer and/or the guidewire introducer/torquer component 300 may have a rounded or rectangular cross sectional area. The funnel tips 310 of the guidewire introducer and/or the guidewire introducer/torquer 300 may have a smaller cross-sectional area than the main body of the guidewire clamp 100 and may be spaced apart from the main body.

The individual introducer and introducer/torquer components can be an integral part of the guidewire clamp device 100 (FIGS. 4A, 4B) or may be detachable through couplings 500 or clasps 600 and function independently (FIGS. 5A-6B and FIGS. 6A-6B). The individual introducer and introducer/torquer devices 300 may be made available/sold as an independent introducer device or an independent introducer/torque device 300 without the guidewire clamp 100 (FIGS. 7A-12B). A simple introducer 300 (for example, without a torquer function) may be an integral part of the guidewire clamp 100, or be made detachable and function independently.

Also provided may be assemblies and components to grasp a guidewire GW in the introducer devices 300, allowing them to also function as a torquer. Various assemblies and components in various combinations are described below. Such components may include: a screw assembly to compress the jaws, jaws compressible by a screw mechanism, a slider compression assembly which may press against a thin walled compressible elastic memory dilator or an elastic memory membrane (either or both of which may be a metal or a synthetic plastic) to grab the guidewire, by a slider compression assembly, or a thin walled compressible elastic memory dilator which may be pressed against the guidewire by a slider compression assembly. This dilator may be packaged already inserted into the funnel component of the guidewire clamp device, or packaged separately to be better protected until use, when it is slipped into the guidewire lumen of the guidewire clamp device. It may be held securely in place by a ridge that snaps into a corresponding grove in the introducer body. The introducer device 300 may have various cross-sectional shapes such as circular, ovoid, rectangular, square, or triangular, to name a few.

FIGS. 4A and 4B illustrate a guidewire clamp device 100 which may be provided as a single piece device.

FIGS. 5A and 5B illustrate a guidewire clamp device 100 which may be provided as a two piece device, with a detachable guidewire introducer and torquer component 300.

FIGS. 6A and 6B illustrate a guidewire clamp device 100 which is provided as a two piece device, with a detachable guidewire introducer and torquer component 300.

FIGS. 7A-7D illustrate a slider 400 and an elastic memory membrane assembly 700 to grab the guidewire GW to serve as the introducer/torque device 300. The elastic memory membrane 700 can provide a continuous uninterrupted path for the guidewire GW (including curved tipped and other guidewires) free of obstruction. The slider compression assembly 400 may comprise a "click stop" so the button of the slider compression assembly 400 may be pressed to lock the membrane 700.

FIGS. 8A-8D illustrate a slider 400 and a thin walled compressible elastic memory dilator 800 to grab the guidewire to serve as the introducer/torque device 300. The thin walled compressible elastic memory dilator 300 can provide a continuous uninterrupted path for the guidewire GW (including curved tipped and other guidewires) free of obstruction.

Figure 9A:
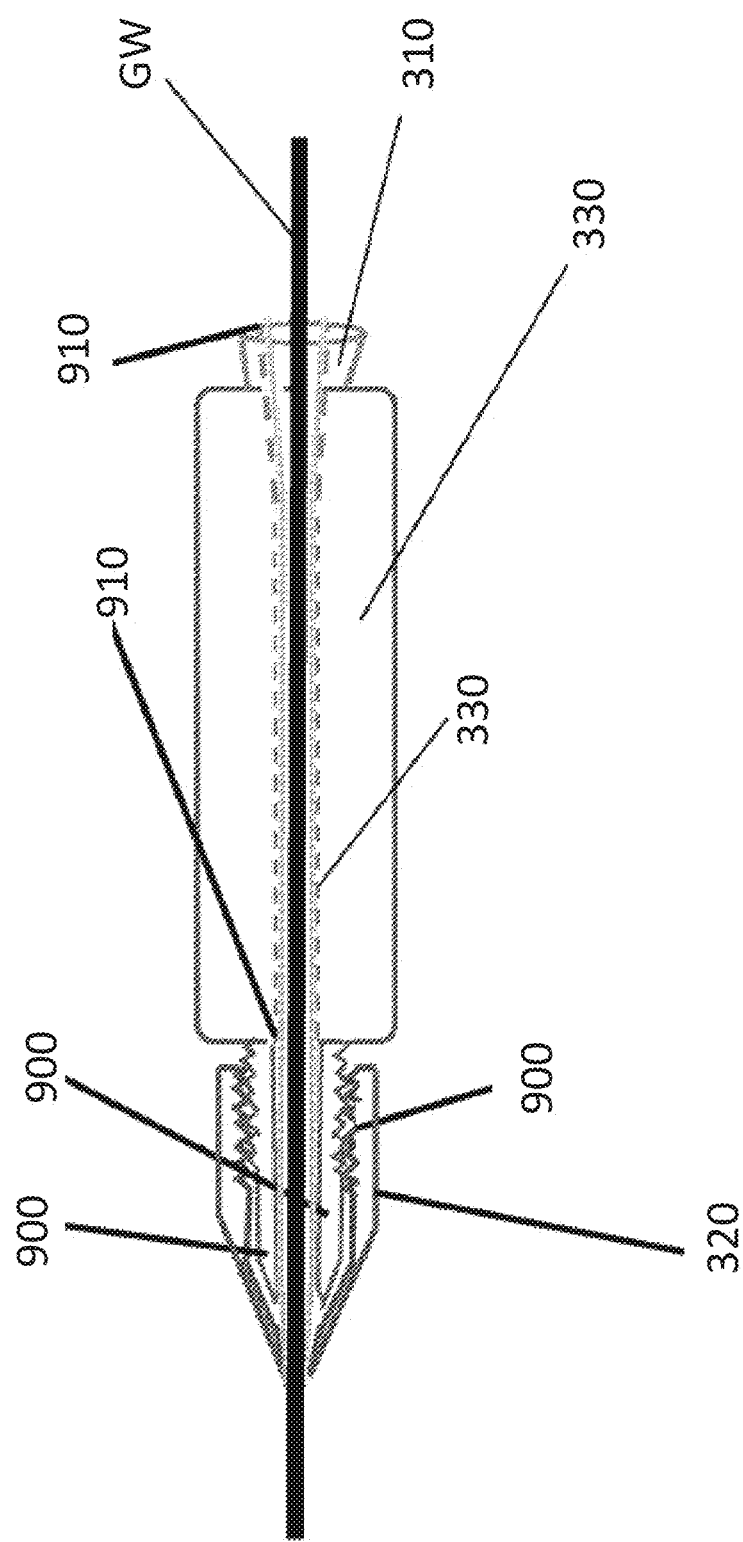
FIG. 9A shows a top section view of another guidewire introducer funnel and torquer in an open configuration, according to many embodiments.
Figure 9B:
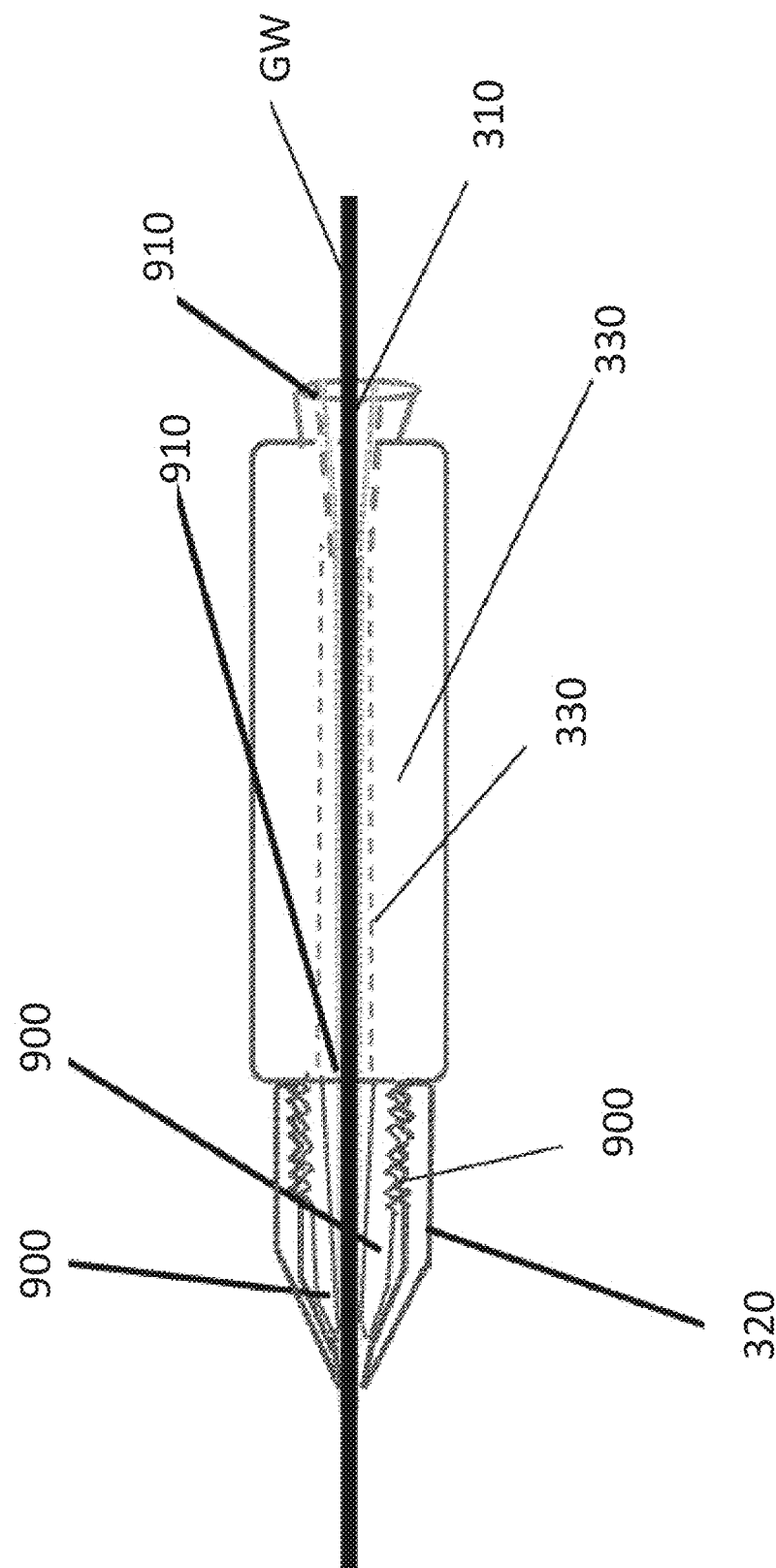
FIG. 9B shows a top section view of the guidewire introducer funnel and torquer of FIG. 9A in a closed configuration.

FIGS. 9A-9B illustrate a screw/jaws assembly 900 in the introducer tip 320 and a thin walled compressible elastic memory dilator 910 to grab the guidewire GW to serve as the introducer/torque device 300. The thin walled compressible elastic memory dilator 900 can provide a continuous uninterrupted path for the guidewire GW (including curved tipped and other guidewires) free of obstruction. The thin walled compressible elastic dilator 910 may be glued to the full length of the introducer/torque body guidewire lumen 330.

Figure 10A:
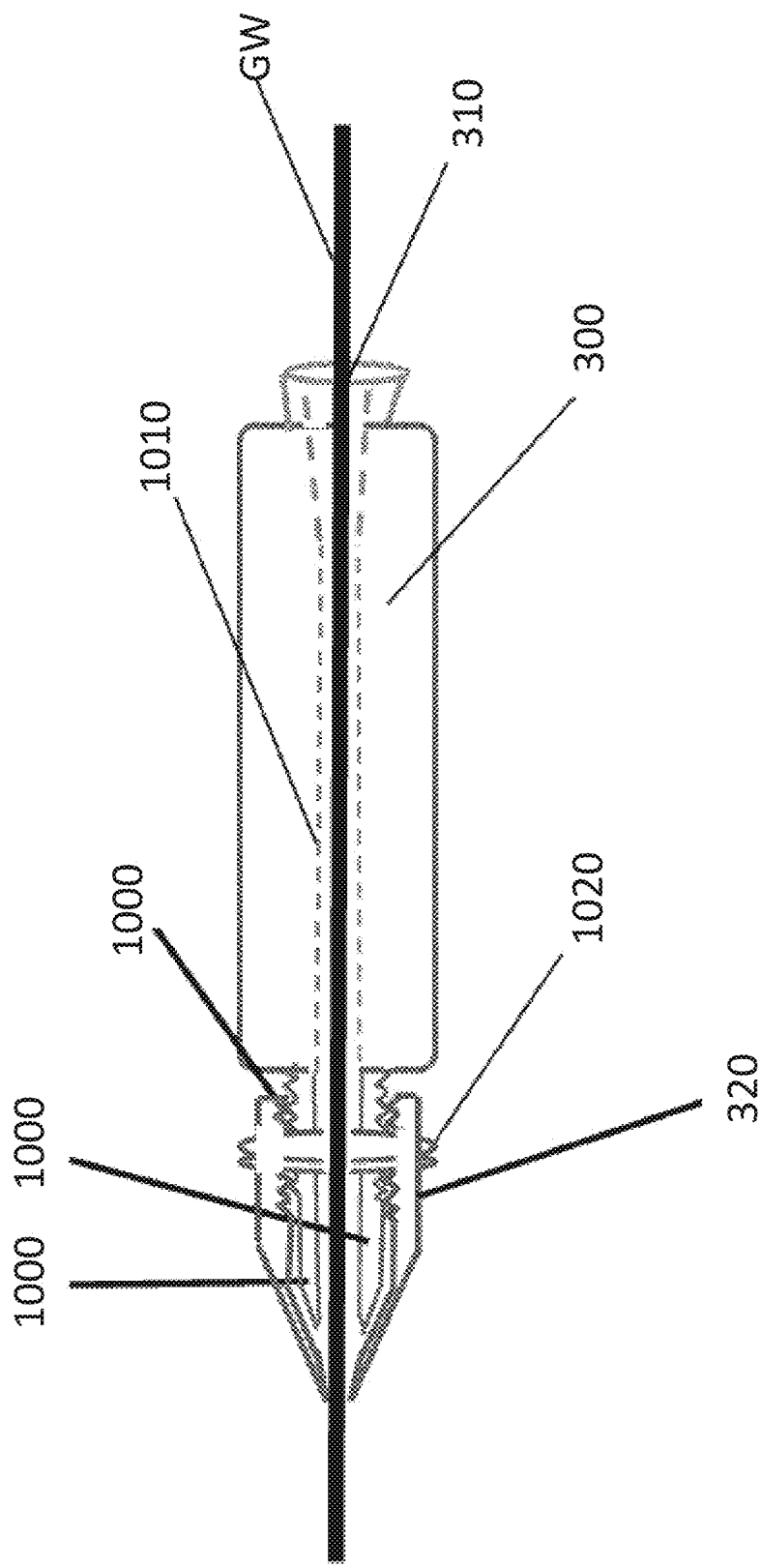
FIG. 10A shows a top section view of another guidewire introducer funnel and torquer in an open configuration, according to many embodiments.
Figure 10B:
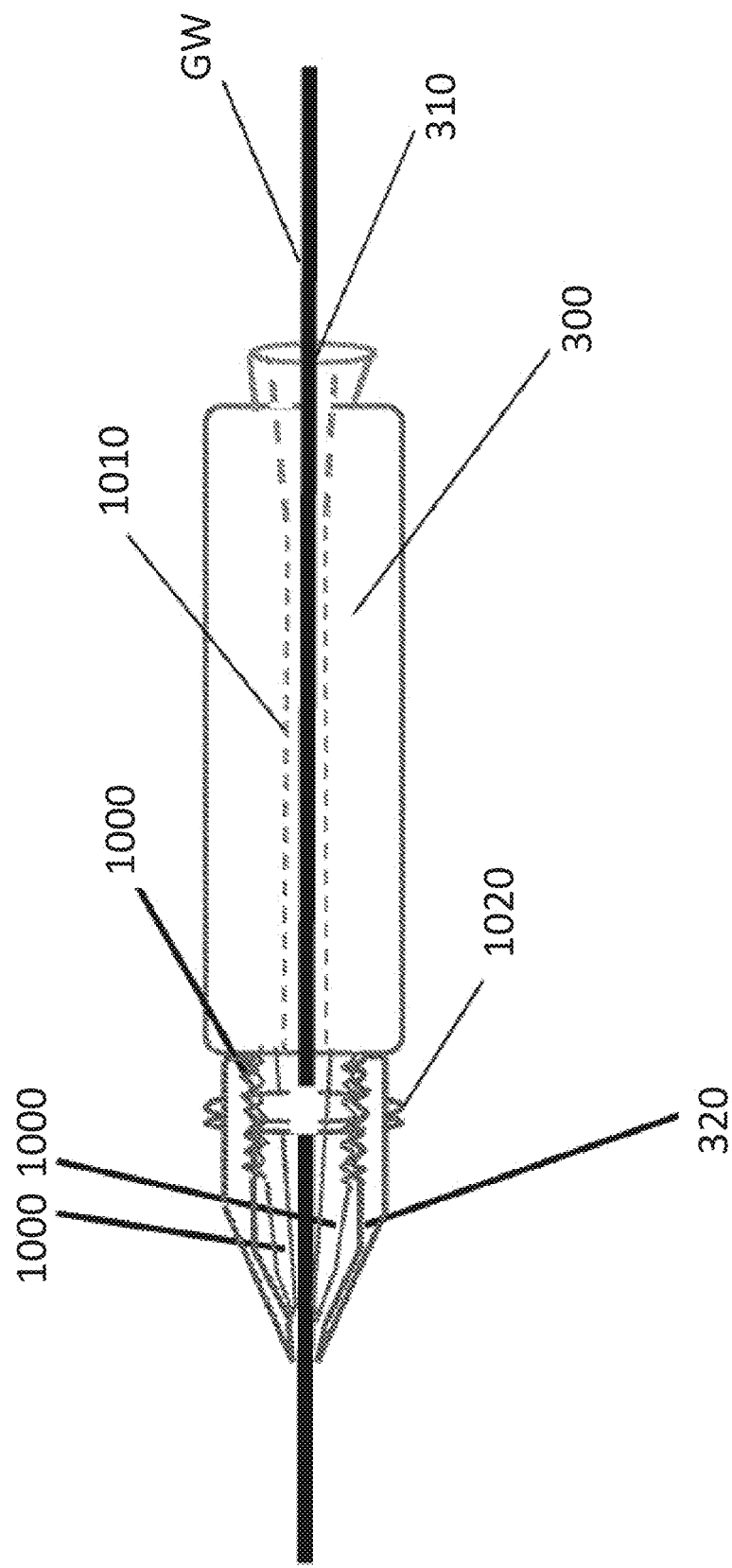
FIG. 10B shows a top section view of the guidewire introducer funnel and torquer of FIG. 10A in a closed configuration.

FIGS. 10A and 10B illustrate a screw/jaws assembly 1000 in the introducer tip 310 and a thin walled compressible elastic memory dilator 1010 to grab the guidewire GW to serve as the introducer/torque device 300. The thin walled compressible elastic memory dilator 1010 can provide a continuous uninterrupted path for the guidewire GW (including curved tipped and other guidewires) free of obstruction. The screw/jaws assembly 1000 may comprise a knurled knob 1020 to turn the funnel body into the screw jaws assembly 1000 and thereby tighten the jaws to "grab" the guidewire GW.

Figure 11A:
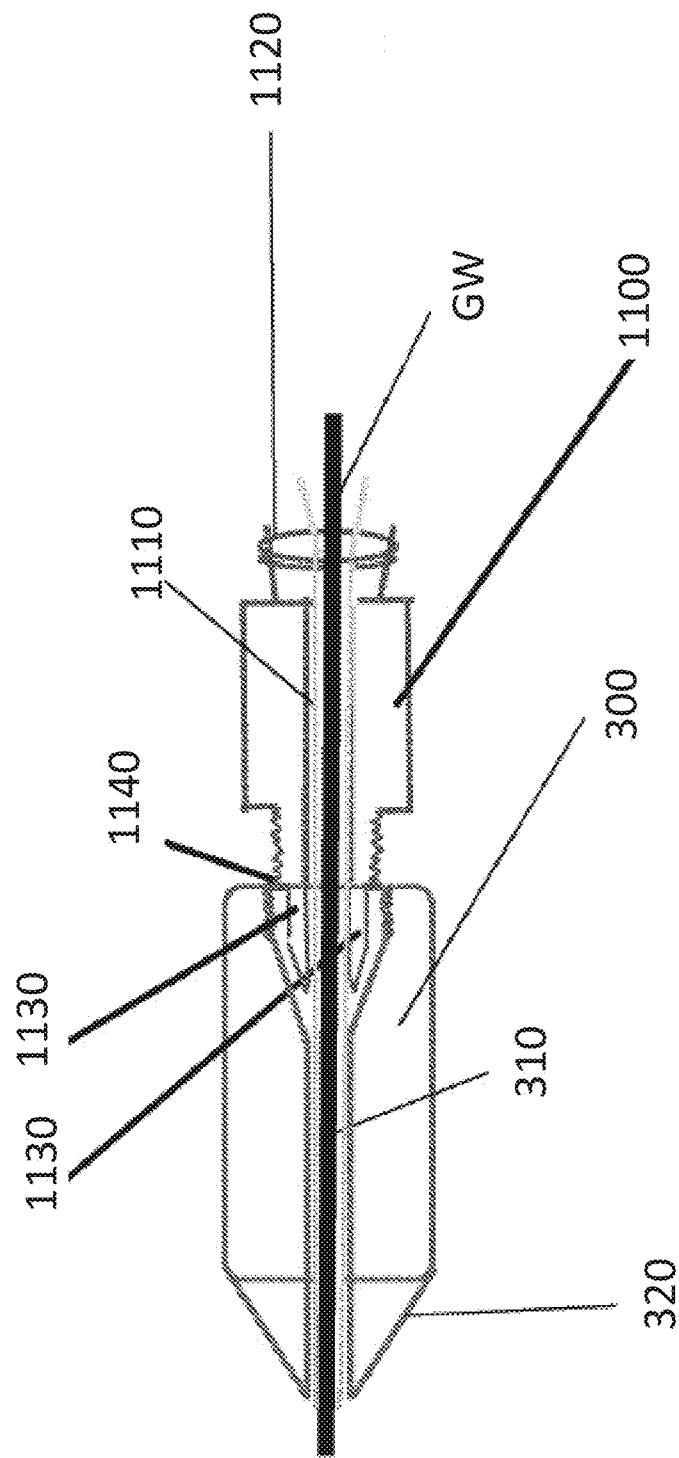
FIG. 11A shows a top section view of another guidewire introducer funnel and torquer in an open configuration, according to many embodiments.
Figure 11B:
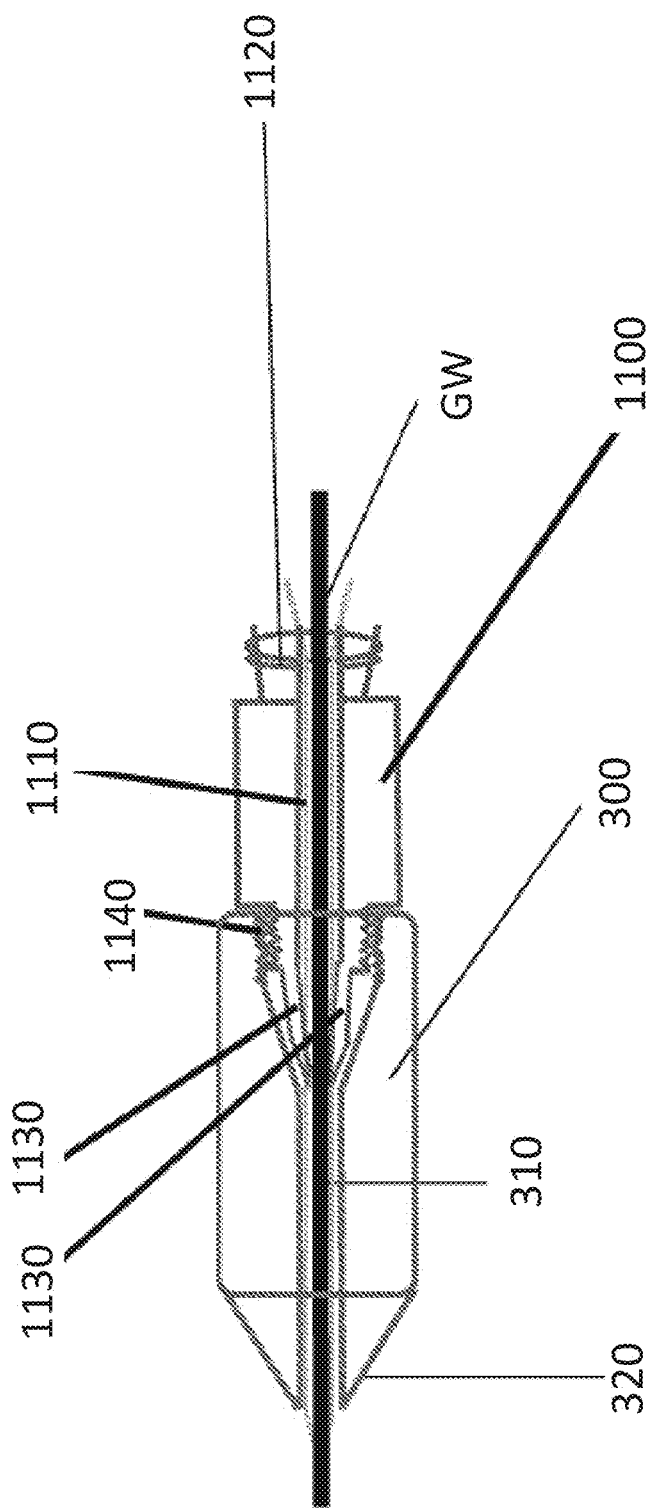
FIG. 11B shows a top section view of the guidewire introducer funnel and torquer of FIG. 11A in a closed configuration.

FIGS. 11A and 11B illustrate a screw/jaws assembly 1100 in the funnel to grab the guidewire GW to serve as an introducer/torquer device 300. The screw/jaws assembly 1100 may comprise a thin walled compressible elastic memory dilator 1110, a knurled knob 1120 to turn the screw-jaws assembly 1100 into the funnel body 300 and thereby tighten the jaws to "grab" the guidewire GW, sets of jaws 1130, and a screw 1140 to interface with the jaws 1130.

Figure 12A:
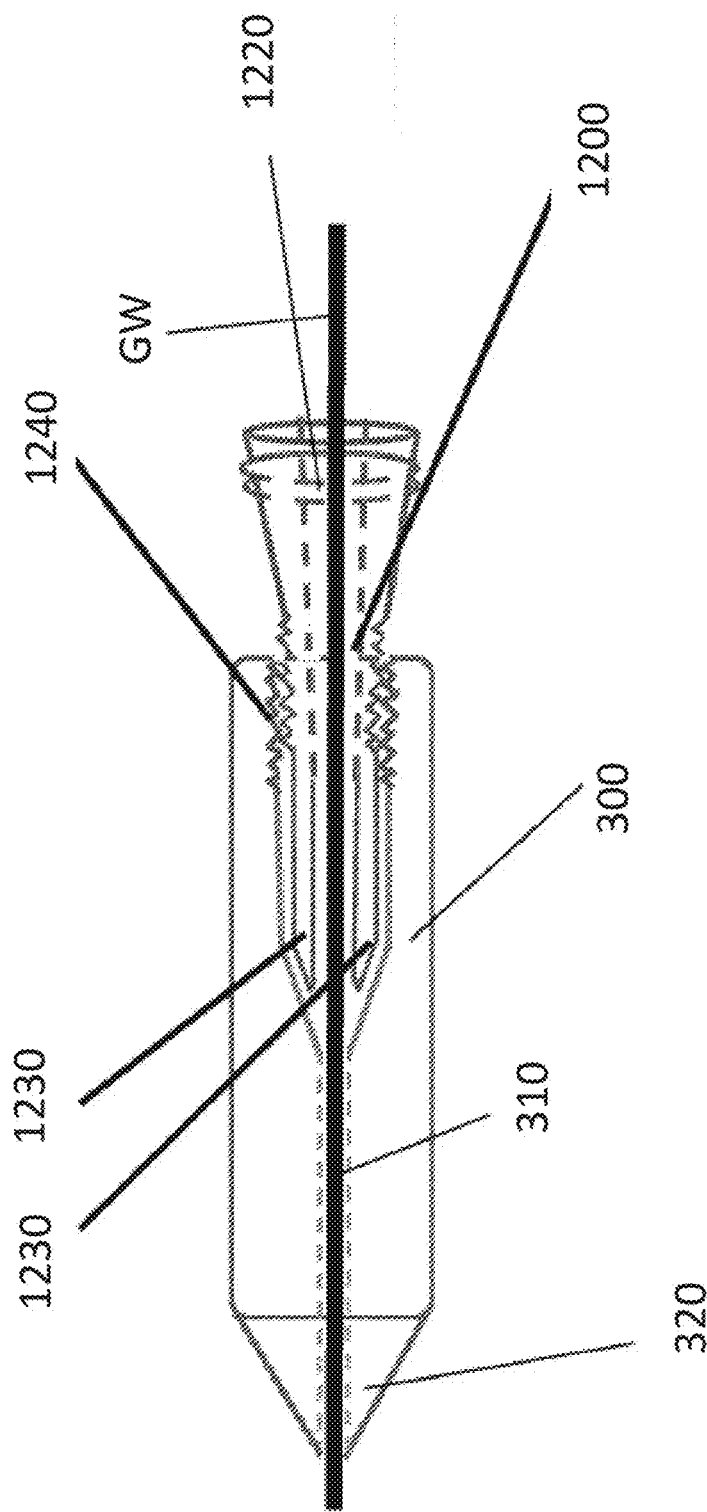
FIG. 12A shows a top section view of another guidewire introducer funnel and torquer in an open configuration, according to many embodiments.
Figure 12B:
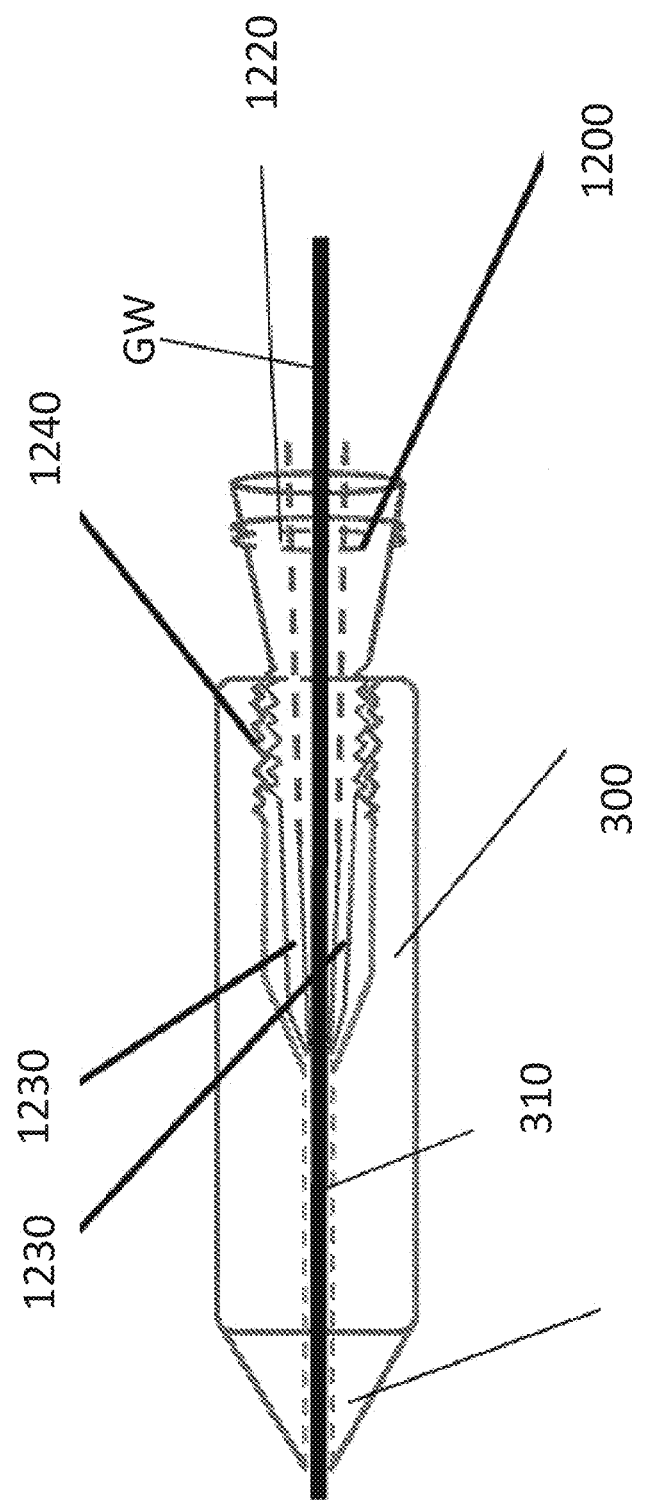
FIG. 12B shows a top section view of the guidewire introducer funnel and torquer of FIG. 12A in a closed configuration.

FIGS. 12A and 12B illustrate a screw/jaws assembly 1200 in the funnel to grab the guidewire GW to serve as an introducer/torque device 300. The screw/jaws assembly 1200 may comprise a knurled knob 1220 to turn the screw-jaws assembly 1200 into the funnel body 300 and thereby tighten the jaws to "grab" the guidewire GW, sets of jaws 1230, and a screw 1240 to interface with the jaws 1230.

Figure 13A:
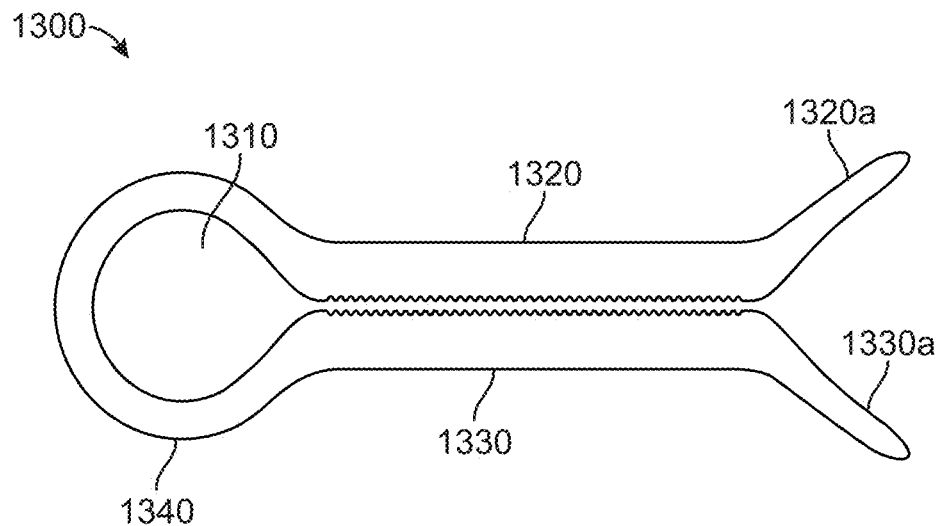
FIG. 13A shows a side view of another guidewire clamp in a closed configuration, according to many embodiments.
Figure 13B:
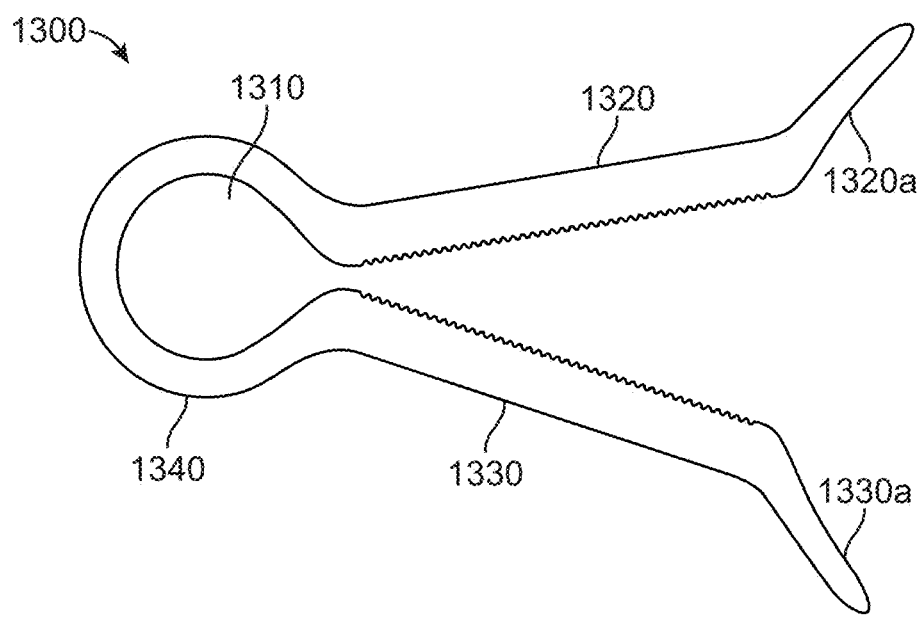
FIG. 13B shows a side view of the guidewire clamp of FIG. 13A in an open configuration.

Referring now to FIGS. 13A and 13B, a guidewire clamp 1300 may define an opening 1310 through which a separate guidewire introducer/torquer 300 may be grasped. The guidewire clamp 1300 may comprise a first toothed jaw 1320 and a second toothed jaw 1330, each with graspable ends 1320a, 1330a, respectively, which may extend outward to be manipulated. The guidewire clamp 1300 may further comprise a flexible middle portion 1340 which the first and second toothed jaws 1320 and 1330 can pivot about. In many embodiments, the guidewire clamp 1300 is biased to be in the closed position shown by FIG. 13A.

Figure 14:
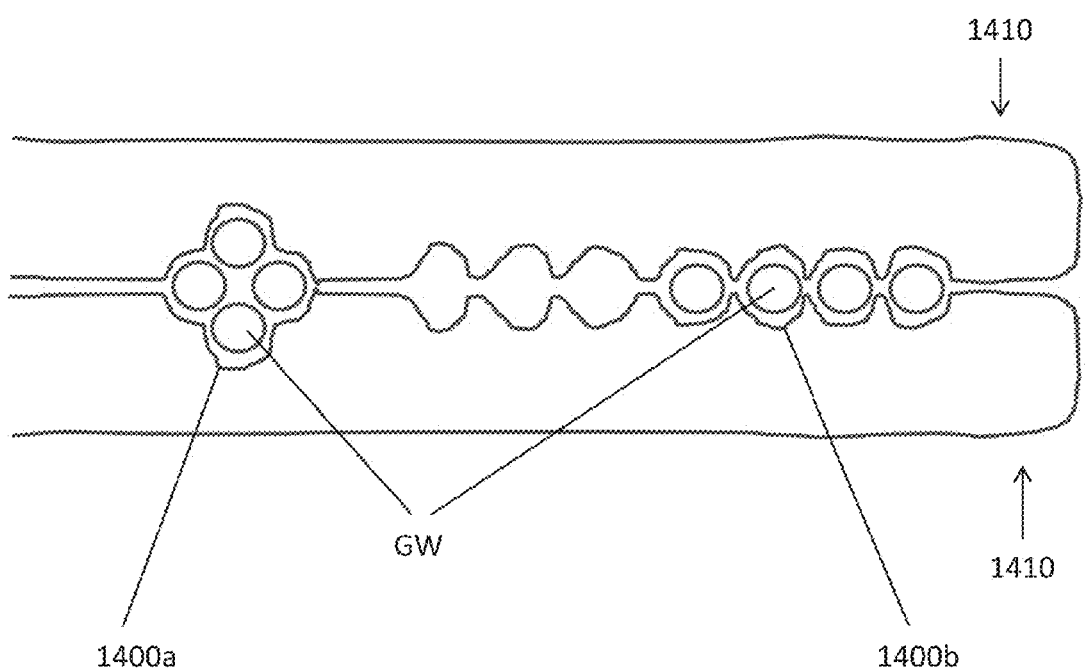
FIG. 14 shows a cross-sectional view of teeth configurations for a guidewire clamp, according to many embodiments.

Referring to FIG. 14, the jaws 1410 of the guidewire clamps may interface with one another in many ways to graph a guidewire GW. For example, teeth 1400a may comprise semi-circular cut-outs which define a passageway sized and shaped to bundle of loops of the guidewire GW when the jaws are closed. Alternatively or in combination, teeth 1400b may comprise linear teeth with complimentary pairs of teeth defining a passageway for a single loop of the guidewire GW such that the loops of the guidewire GW are spread linearly side to side.

FIG. 15 shows a guidewire claim 1500. The guidewire clamp 1500 may comprise a plurality of ribs 1510. Loops of the guidewire GW may be held in-between the ribs 1510. The guidewire clamp 1500 may comprise a gap 1520. The guidewire clamp 1500 may further comprise end tabs 1530a and 1530b, and the end tab 1530a may be advanced through the gap 1520 (FIG. 15C.) One or more of the ribs 1510 may facilitate closure and locking of the end tab 1530a through the gap 1520 (FIG. 15C.) The guidewire clamp 1500 may be flexible such that the end tab 1530a may be bent, pulled, or otherwise manipulated in the manner shown (FIGS. 15B, 15C.)

Referring to FIGS. 16A and 16B, the guidewire clamps described herein may be constructed of a crushable, "thin" membrane 1600. The crushable "thin" membrane may cover the teeth 1400a and/or the teeth 1400b of the jaw 1410. The crushable, "thin" membrane 1600 may be deformed by the coils of the guidewire and may a traumatically "mold" around the coils to secure them in the semi-circular openings of the teeth 1400a and/or the teeth 1400b. The crushable, "thin" membrane 1600 may be molded as part of the entire clamp of the same material, may be present in the entire "semicircle" (teeth 1400a and/or teeth 1400b) of the jaw 1410, may reach only part way from the trough of the teeth 1400a and/or the teeth 1400b to the edge of the jaw 1410, and/or may be present in both the upper and lower jaws or in just one.

While preferred embodiments of the present disclosure have been shown and described herein, it will be obvious to those skilled in the art that such embodiments are provided by way of example only. Numerous variations, changes, and substitutions will now occur to those skilled in the art without departing from the spirit of the present disclosure. It should be understood that various alternatives to the embodiments of the present disclosure described herein may be employed in practicing the present disclosure. It is intended that the following claims define the scope of the invention and that methods and structures within the scope of these claims and their equivalents be covered thereby.

What is claimed is:

1. A clamp for facilitating guidewire storage, the clamp comprising:
    a first portion, a second portion, and a pivotable portion therebetween,
    wherein the first and second portions are foldable or pivotable relative to one another about the pivotable portion to open or close the clamp, and
    wherein the first and second portions comprise upper surfaces configured to approximate or contact one another when the clamp is closed, the upper surfaces having one or more surface features to facilitate capture of the guidewire between the upper surfaces of the first and second portions,
    wherein the one or more surface features comprise teeth, ridges, or ribs to facilitate capture of one or more guidewire loops when the clamp is closed,
    wherein one or more of the first or second portions comprise one or more teeth, wherein the one or more teeth are shaped to accommodate one or more guidewire loops,
    wherein the one or more surface features comprise a high friction material or coating, and
    wherein the high friction material or coating is soft and compliant so as to minimize damage to a guidewire captured between the first and second portions.

2. The clamp of claim 1, wherein the first portion comprises a first set of teeth and the second portion comprises a second set of teeth, the first and second sets being complementary to one another.

3. The clamp of claim 2, wherein the first and second set of teeth fit within one another when the first and second portions are folded to close the clamp.

4. The clamp of claim 2, wherein tips of the first and second set of teeth abut one another when the first and second portions are folded to close the clamp.

5. The clamp of claim 1, wherein the one or more teeth shaped to accommodate one or more guidewire loops comprises a plurality of cut-outs arranged in series, each cut-out being configured to accommodate a single guidewire loop.

6. The clamp of claim 1, wherein the one or more teeth shaped to accommodate the one or more guidewire loops comprises a cut-out having a plurality of semi-circular sections, the cut-out being configured to accommodate a plurality of guidewire loops.

7. The clamp of claim 1, further comprising a first end coupled to the first portion and a second end coupled to the second portion, the first and second ends being removably coupleable to one another.

8. The clamp of claim 7, wherein the first end comprises one or more teeth to capture the second end when the first and second portions are folded or pivoted relative to one another to close the clamp.

9. The clamp of claim 1, further comprising a guidewire introducer coupled to one or more of the first or second portions, wherein the guidewire introducer has a guidewire lumen, an open proximal end to receive a guidewire and direct the guidewire into the guidewire lumen, and a distal funnel tip to couple with a proximal hub of a catheter.

10. The clamp of claim 9, wherein the guidewire introducer further comprises a grasping mechanism to secure the guidewire received in the guidewire lumen.

11. The clamp of claim 9, wherein the guidewire introducer is removably coupled to one or more of the first or second portions.

12. A clamp for facilitating guidewire storage, the clamp comprising:
    a first portion, a second portion, and a pivotable portion therebetween,
    wherein the first and second portions are foldable or pivotable relative to one another about the pivotable portion to open or close the clamp,
    wherein the first and second portions comprise upper surfaces configured to approximate or contact one another when the clamp is closed, the upper surfaces having one or more surface features to facilitate capture of the guidewire between the upper surfaces of the first and second portions,
    wherein the one or more surface features comprise teeth, ridges, or ribs to facilitate capture of one or more guidewire loops when the clamp is closed,
    wherein one or more of the first or second portions comprise one or more teeth,
    wherein the one or more teeth are shaped to accommodate one or more guidewire loops,
    wherein the one or more teeth shaped to accommodate the one or more guidewire loops comprises a cut-out having a plurality of semi-circular sections, the cut-out being configured to accommodate a plurality of guidewire loops, and
    wherein the clamp further comprises a soft membrane over at least a portion of the cut-out.

13. The clamp of claim 12, wherein the first portion comprises a first set of teeth and the second portion comprises a second set of teeth, the first and second sets being complementary to one another.

14. The clamp of claim 13, wherein the first and second set of teeth fit within one another when the first and second portions are folded to close the clamp.

15. The clamp of claim 13, wherein tips of the first and second set of teeth abut one another when the first and second portions are folded to close the clamp.

16. The clamp of claim 12, wherein a portion of the one or more teeth shaped to accommodate one or more guidewire loops comprises a plurality of cut-outs arranged in series, each cut-out being configured to accommodate a single guidewire loop.

17. The clamp of claim 12, wherein the soft membrane comprises a high friction material or coating.

18. The clamp of claim 12, wherein the high friction material or coating is soft and compliant so as to minimize damage to a guidewire captured between the first and second portions.

19. The clamp of claim 12, further comprising a first end coupled to the first portion and a second end coupled to the second portion, the first and second ends being removably coupleable to one another.

20. The clamp of claim 19, wherein the first end comprises one or more teeth to capture the second end when the first and second portions are folded or pivoted relative to one another to close the clamp.

21. The clamp of claim 12, further comprising a guidewire introducer coupled to one or more of the first or second portions, wherein the guidewire introducer has a guidewire lumen, an open proximal end to receive a guidewire and direct the guidewire into the guidewire lumen, and a distal funnel tip to couple with a proximal hub of a catheter.

22. The clamp of claim 21, wherein the guidewire introducer further comprises a grasping mechanism to secure the guidewire received in the guidewire lumen.

23. The clamp of claim 21, wherein the guidewire introducer is removably coupled to one or more of the first or second portions.

\* \* \* \* \*